(12) United States Patent
Simpson et al.

(10) Patent No.: US 11,944,342 B2
(45) Date of Patent: Apr. 2, 2024

(54) IDENTIFICATION OF ELASTIC LAMINA TO GUIDE INTERVENTIONAL THERAPY

(71) Applicant: Avinger, Inc., Redwood City, CA (US)

(72) Inventors: John B. Simpson, Woodside, CA (US); Xuanmin He, Sunnyvale, CA (US); Ryan Radjabi, Campbell, CA (US); Richard R. Newhauser, Redwood City, CA (US)

(73) Assignee: Avinger, Inc., Redwood City, CA (US)

( * ) Notice: Subject to any disclaimer, the term of this patent is extended or adjusted under 35 U.S.C. 154(b) by 353 days.

(21) Appl. No.: 17/075,548

(22) Filed: Oct. 20, 2020

(65) Prior Publication Data

US 2021/0267621 A1    Sep. 2, 2021

Related U.S. Application Data

(63) Continuation of application No. 16/194,183, filed on Nov. 16, 2018, now Pat. No. 10,806,484, which is a
(Continued)

(51) Int. Cl.
| | |
|---|---|
| *A61B 17/3207* | (2006.01) |
| *A61B 17/00* | (2006.01) |
| *A61B 17/22* | (2006.01) |
| *A61B 34/10* | (2016.01) |
| *A61B 90/00* | (2016.01) |

(52) U.S. Cl.
CPC .. *A61B 17/3207* (2013.01); *A61B 17/320783* (2013.01); *A61B 90/361* (2016.02); *A61B 2017/00119* (2013.01); *A61B 2017/22071* (2013.01); *A61B 2017/320791* (2013.01);
(Continued)

(58) Field of Classification Search
CPC ........ A61B 17/3207; A61B 17/320716; A61B 17/32075; A61B 17/320758; A61B 2017/320741; A61B 2017/320766; A61B 2017/320791; A61B 90/361; A61B 2090/3612; A61B 2090/3614; A61B 2090/3616; A61B 2090/3618; A61B 2090/3735; A61B 2034/107; A61F 2/07;
(Continued)

(56) References Cited

U.S. PATENT DOCUMENTS

| | | |
|---|---|---|
| 3,367,727 A | 2/1968 | Ward et al. |
| 3,908,637 A | 9/1975 | Doroshow |

(Continued)

FOREIGN PATENT DOCUMENTS

| | | |
|---|---|---|
| CN | 1875242 A | 12/2006 |
| CN | 1947652 A | 4/2007 |

(Continued)

OTHER PUBLICATIONS

Patel et al.; U.S. Appl. No. 17/816,673 entitled "Atherectomy catheter with serrated cutter," filed Aug. 1, 2022.
(Continued)

*Primary Examiner* — Wade Miles
(74) *Attorney, Agent, or Firm* — Shay Glenn LLP

(57) ABSTRACT

Described herein is a system and method for identifying elastic lamina during interventional procedures, such as atherectomy. Such identification can be used to avoid trauma to the external elastic lamina during the procedure.

11 Claims, 32 Drawing Sheets

Related U.S. Application Data continuation of application No. 14/899,893, filed as application No. PCT/US2014/045799 on Jul. 8, 2014, now Pat. No. 10,130,386.

(60) Provisional application No. 61/843,866, filed on Jul. 8, 2013.

(52) U.S. Cl.
CPC .............. *A61B 2034/107* (2016.02); *A61B 2090/08021* (2016.02); *A61B 2090/3735* (2016.02)

(58) Field of Classification Search
CPC .......... A61F 2002/072; A61F 2002/075; A61F 2002/077
See application file for complete search history.

(56) References Cited

U.S. PATENT DOCUMENTS

| | | |
|---|---|---|
| 4,178,935 A | 12/1979 | Gekhaman et al. |
| 4,487,206 A | 12/1984 | Aagard |
| 4,527,553 A | 7/1985 | Upsher |
| 4,552,554 A | 11/1985 | Gould et al. |
| 4,578,061 A | 3/1986 | Lemelson |
| 4,598,710 A | 7/1986 | Kleinberg et al. |
| 4,611,600 A | 9/1986 | Cohen |
| 4,621,353 A | 11/1986 | Hazel et al. |
| 4,639,091 A | 1/1987 | Huignard et al. |
| 4,651,753 A | 3/1987 | Lifton |
| 4,654,024 A | 3/1987 | Crittenden et al. |
| 4,681,106 A | 7/1987 | Kensey et al. |
| 4,686,982 A | 8/1987 | Nash |
| 4,691,708 A | 9/1987 | Kane |
| 4,729,763 A | 3/1988 | Henrie |
| 4,771,774 A | 9/1988 | Simpson et al. |
| 4,781,186 A | 11/1988 | Simpson et al. |
| 4,808,163 A | 2/1989 | Laub |
| 4,841,977 A | 6/1989 | Griffith et al. |
| 4,842,578 A | 6/1989 | Johnson et al. |
| 4,850,354 A | 7/1989 | McGurk-Burleson et al. |
| 4,857,046 A | 8/1989 | Stevens et al. |
| 4,920,961 A | 5/1990 | Grossi et al. |
| 4,926,858 A | 5/1990 | Gifford et al. |
| 5,000,185 A | 3/1991 | Yock |
| 5,002,560 A | 3/1991 | Machold et al. |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,217,479 A | 6/1993 | Shuler |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,372,601 A | 12/1994 | Lary |
| 5,383,460 A | 1/1995 | Jang et al. |
| 5,383,467 A | 1/1995 | Auer et al. |
| 5,425,273 A | 6/1995 | Chevalier |
| 5,425,371 A | 6/1995 | Mischenko |
| 5,429,136 A | 7/1995 | Milo et al. |
| 5,431,673 A | 7/1995 | Summers et al. |
| 5,437,284 A | 8/1995 | Trimble |
| 5,449,372 A | 9/1995 | Schmaltz et al. |
| 5,459,570 A | 10/1995 | Swanson et al. |
| 5,460,168 A | 10/1995 | Masubuchi et al. |
| 5,465,147 A | 11/1995 | Swanson |
| 5,507,725 A | 4/1996 | Savage et al. |
| 5,507,760 A | 4/1996 | Wynne et al. |
| 5,507,795 A | 4/1996 | Chiang et al. |
| 5,517,998 A | 5/1996 | Madison |
| 5,529,580 A | 6/1996 | Kusunok et al. |
| 5,556,405 A | 9/1996 | Lary |
| 5,607,394 A | 3/1997 | Andersen et al. |
| 5,613,981 A * | 3/1997 | Boyle ................ A61F 2/07 606/198 |
| 5,620,426 A | 4/1997 | Braithwaite |
| 5,632,754 A | 5/1997 | Farley et al. |
| 5,632,755 A | 5/1997 | Nordgren et al. |
| 5,667,490 A | 9/1997 | Keith et al. |
| 5,674,232 A | 10/1997 | Halliburton |
| 5,676,012 A | 10/1997 | Ceriale |
| 5,681,336 A | 10/1997 | Clement et al. |
| 5,690,634 A | 11/1997 | Muller et al. |
| 5,722,403 A | 3/1998 | McGee et al. |
| 5,728,148 A | 3/1998 | Bostrom et al. |
| 5,749,846 A | 5/1998 | Edwards et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,851,212 A | 12/1998 | Zirps et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,935,139 A | 8/1999 | Bates |
| 5,938,602 A | 8/1999 | Lloyd |
| 5,938,671 A | 8/1999 | Katoh et al. |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Domhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,285,903 B1 | 9/2001 | Rosenthal et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,375,615 B1 | 4/2002 | Flaherty et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |

(56) References Cited

U.S. PATENT DOCUMENTS

| | | | |
|---|---|---|---|
| 6,451,009 B1 * | 9/2002 | Dasilva | A61B 18/20 606/11 |
| 6,451,036 B1 | 9/2002 | Heitzmann et al. | |
| 6,454,717 B1 | 9/2002 | Pantages et al. | |
| 6,454,779 B1 | 9/2002 | Taylor | |
| 6,482,216 B1 | 11/2002 | Hiblar et al. | |
| 6,482,217 B1 | 11/2002 | Pintor et al. | |
| 6,485,413 B1 | 11/2002 | Boppart et al. | |
| 6,497,649 B2 | 12/2002 | Parker et al. | |
| 6,501,551 B1 | 12/2002 | Teamney et al. | |
| 6,503,261 B1 | 1/2003 | Bruneau et al. | |
| 6,511,458 B2 | 1/2003 | Milo et al. | |
| 6,517,528 B1 | 2/2003 | Pantages et al. | |
| 6,542,665 B2 | 4/2003 | Reed et al. | |
| 6,544,230 B1 | 4/2003 | Flaherty et al. | |
| 6,546,272 B1 | 4/2003 | MacKinnon et al. | |
| 6,551,302 B1 | 4/2003 | Rosinko et al. | |
| 6,563,105 B2 | 5/2003 | Seibel et al. | |
| 6,564,087 B1 | 5/2003 | Pitris et al. | |
| 6,565,588 B1 | 5/2003 | Clement et al. | |
| 6,572,563 B2 | 6/2003 | Ouchi et al. | |
| 6,572,643 B1 | 6/2003 | Gharibadeh | |
| 6,575,995 B1 | 6/2003 | Huter et al. | |
| 6,579,298 B1 | 6/2003 | Bruneau et al. | |
| 6,599,296 B1 | 7/2003 | Gillick et al. | |
| 6,615,071 B1 | 9/2003 | Casscells, III et al. | |
| 6,629,953 B1 | 10/2003 | Boyd | |
| 6,638,233 B2 | 10/2003 | Corvi et al. | |
| 6,645,217 B1 | 11/2003 | MacKinnon et al. | |
| 6,657,727 B1 | 12/2003 | Izatt et al. | |
| 6,666,874 B2 | 12/2003 | Heitzmann et al. | |
| 6,673,042 B1 | 1/2004 | Samson et al. | |
| 6,687,010 B1 | 2/2004 | Horii | |
| 6,728,571 B1 | 4/2004 | Barbato | |
| D489,973 S | 5/2004 | Root et al. | |
| 6,730,063 B2 | 5/2004 | Delaney et al. | |
| 6,758,854 B1 | 7/2004 | Butler et al. | |
| 6,760,112 B2 | 7/2004 | Reed et al. | |
| 6,800,085 B2 | 10/2004 | Selmon et al. | |
| 6,818,001 B2 | 11/2004 | Wulfman et al. | |
| 6,824,550 B1 | 11/2004 | Noriega et al. | |
| 6,830,577 B2 | 12/2004 | Nash et al. | |
| 6,845,190 B1 | 1/2005 | Smithwick et al. | |
| 6,852,109 B2 | 2/2005 | Winston et al. | |
| 6,853,457 B2 | 2/2005 | Bjarklev et al. | |
| 6,856,712 B2 | 2/2005 | Fauver et al. | |
| 6,867,753 B2 | 3/2005 | Chinthammit et al. | |
| 6,879,851 B2 | 4/2005 | McNamara et al. | |
| 6,947,787 B2 | 9/2005 | Webler | |
| 6,961,123 B1 | 11/2005 | Wang et al. | |
| 6,970,732 B2 | 11/2005 | Winston et al. | |
| 6,975,898 B2 | 12/2005 | Seibel | |
| 7,068,878 B2 | 6/2006 | Crossman-Bosworth et al. | |
| 7,074,231 B2 | 7/2006 | Jang | |
| 7,126,693 B2 | 10/2006 | Everett et al. | |
| 7,172,610 B2 | 2/2007 | Heitzmann et al. | |
| 7,242,480 B2 | 7/2007 | Alphonse | |
| 7,261,687 B2 | 8/2007 | Yang | |
| 7,288,087 B2 | 10/2007 | Winston et al. | |
| 7,291,146 B2 * | 11/2007 | Steinke | A61B 18/1492 606/41 |
| 7,297,131 B2 | 11/2007 | Nita | |
| 7,311,723 B2 | 12/2007 | Seibel et al. | |
| 7,344,546 B2 | 3/2008 | Wulfman et al. | |
| 7,366,376 B2 | 4/2008 | Shishkov et al. | |
| 7,382,949 B2 | 6/2008 | Bouma et al. | |
| 7,426,036 B2 | 9/2008 | Feldchtein et al. | |
| 7,428,001 B2 | 9/2008 | Schowengerdt et al. | |
| 7,428,053 B2 | 9/2008 | Feldchtein et al. | |
| 7,455,649 B2 | 11/2008 | Root et al. | |
| 7,474,407 B2 | 1/2009 | Gutin | |
| 7,485,127 B2 | 2/2009 | Nistal | |
| 7,488,340 B2 | 2/2009 | Kauphusman et al. | |
| 7,530,948 B2 | 5/2009 | Seibel et al. | |
| 7,530,976 B2 | 5/2009 | MacMahon et al. | |
| 7,538,859 B2 | 5/2009 | Tearney et al. | |
| 7,538,886 B2 | 5/2009 | Feldchtein | |
| 7,539,362 B2 | 5/2009 | Teramura | |
| 7,542,145 B2 | 6/2009 | Toida et al. | |
| 7,544,162 B2 | 6/2009 | Ohkubo | |
| 7,545,504 B2 | 6/2009 | Buckland et al. | |
| 7,555,333 B2 | 6/2009 | Wang et al. | |
| 7,577,471 B2 | 8/2009 | Camus et al. | |
| 7,583,872 B2 | 9/2009 | Seibel et al. | |
| 7,616,986 B2 | 11/2009 | Seibel et al. | |
| 7,637,885 B2 | 12/2009 | Maschke | |
| 7,674,253 B2 | 3/2010 | Fisher et al. | |
| 7,682,319 B2 | 3/2010 | Martin et al. | |
| 7,706,863 B2 | 4/2010 | Imanishi et al. | |
| 7,728,985 B2 | 6/2010 | Feldchtein et al. | |
| 7,729,745 B2 | 6/2010 | Maschke | |
| 7,734,332 B2 | 6/2010 | Sher | |
| 7,738,945 B2 | 6/2010 | Fauver et al. | |
| 7,753,852 B2 | 7/2010 | Maschke | |
| 7,771,425 B2 | 8/2010 | Dycus et al. | |
| 7,776,062 B2 | 8/2010 | Bessellink et al. | |
| 7,785,286 B2 | 8/2010 | Magnin et al. | |
| 7,813,609 B2 | 10/2010 | Petersen et al. | |
| 7,821,643 B2 | 10/2010 | Amazeen et al. | |
| 7,824,089 B2 | 11/2010 | Charles | |
| 7,840,283 B1 | 11/2010 | Bush et al. | |
| 7,944,568 B2 | 5/2011 | Teramura et al. | |
| 7,952,718 B2 | 5/2011 | Li et al. | |
| 7,972,299 B2 | 7/2011 | Carter et al. | |
| 8,002,763 B2 | 8/2011 | Berthiaume et al. | |
| 8,059,274 B2 | 11/2011 | Splinter | |
| 8,062,316 B2 | 11/2011 | Patel et al. | |
| 8,068,921 B2 | 11/2011 | Prakash et al. | |
| 8,313,493 B2 | 11/2012 | Fisher | |
| 8,361,097 B2 | 1/2013 | Patel et al. | |
| 8,548,571 B2 | 10/2013 | He et al. | |
| 8,548,603 B2 | 10/2013 | Swoyer et al. | |
| 8,632,557 B2 | 1/2014 | Thatcher et al. | |
| 8,644,913 B2 | 2/2014 | Simpson et al. | |
| 8,647,335 B2 | 2/2014 | Markus | |
| 8,696,695 B2 | 4/2014 | Patel et al. | |
| 8,911,459 B2 | 12/2014 | Simpson et al. | |
| 9,119,662 B2 | 9/2015 | Moberg | |
| 9,125,562 B2 | 9/2015 | Spencer et al. | |
| 9,333,007 B2 | 5/2016 | Escudero et al. | |
| 9,345,398 B2 | 5/2016 | Tachibana et al. | |
| 9,345,406 B2 | 5/2016 | Spencer et al. | |
| 9,345,510 B2 | 5/2016 | Patel et al. | |
| 9,345,511 B2 | 5/2016 | Smith et al. | |
| 9,351,757 B2 | 5/2016 | Kusleika | |
| 9,498,247 B2 | 11/2016 | Patel et al. | |
| 9,498,600 B2 | 11/2016 | Rosenthal et al. | |
| 9,557,156 B2 | 1/2017 | Kankaria | |
| 9,572,492 B2 | 2/2017 | Simpson et al. | |
| 9,579,157 B2 | 2/2017 | Moberg | |
| 9,592,075 B2 | 3/2017 | Simpson et al. | |
| 9,642,646 B2 | 5/2017 | Patel et al. | |
| 9,788,790 B2 | 10/2017 | Black et al. | |
| 9,854,979 B2 | 1/2018 | Smith et al. | |
| 9,918,734 B2 | 3/2018 | Patel et al. | |
| 9,949,754 B2 | 4/2018 | Newhauser et al. | |
| 10,052,125 B2 | 8/2018 | Rosenthal et al. | |
| 10,130,386 B2 | 11/2018 | Simpson et al. | |
| 10,213,224 B2 | 2/2019 | Guggenheimer et al. | |
| 10,244,934 B2 | 4/2019 | Tachibana et al. | |
| 10,335,173 B2 | 7/2019 | Carver et al. | |
| 10,342,491 B2 | 7/2019 | Black et al. | |
| 10,349,974 B2 | 7/2019 | Patel et al. | |
| 10,357,277 B2 | 7/2019 | Patel et al. | |
| 10,363,062 B2 | 7/2019 | Spencer et al. | |
| 10,406,316 B2 | 9/2019 | Garvey et al. | |
| 10,470,795 B2 | 11/2019 | Patel et al. | |
| 10,548,478 B2 | 2/2020 | Simpson et al. | |
| 10,568,520 B2 | 2/2020 | Patel et al. | |
| 10,568,655 B2 | 2/2020 | Simpson et al. | |
| 10,722,121 B2 | 7/2020 | Smith et al. | |
| 10,729,326 B2 | 8/2020 | Spencer et al. | |
| 10,806,484 B2 * | 10/2020 | Simpson | A61B 17/3207 |
| 10,860,484 B2 | 12/2020 | McKenna et al. | |

(56) References Cited

U.S. PATENT DOCUMENTS

| | | |
|---|---|---|
| 10,869,685 B2 | 12/2020 | Patel et al. |
| 2001/0005788 A1 | 6/2001 | McGuckin, Jr. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0097400 A1 | 7/2002 | Jung et al. |
| 2002/0111548 A1 | 8/2002 | Swanson et al. |
| 2002/0115931 A1 | 8/2002 | Strauss et al. |
| 2002/0138091 A1 | 9/2002 | Pflueger |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0193140 A1 | 9/2004 | Griffin et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0021075 A1 | 1/2005 | Bonnette et al. |
| 2005/0027199 A1 | 2/2005 | Clarke |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0149096 A1 | 7/2005 | Hilal et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0197623 A1 | 9/2005 | Leeflang et al. |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0050019 A1 | 3/2007 | Hyde |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0167710 A1 | 7/2007 | Unal et al. |
| 2007/0196926 A1 | 8/2007 | Solto et al. |
| 2007/0213618 A1 | 9/2007 | Li et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0015618 A1 | 1/2008 | Sonnenschein et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1 | 6/2008 | O'Sullivan et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0154296 A1 | 6/2008 | Taylor et al. |
| 2008/0177138 A1 | 7/2008 | Courtney et al. |
| 2008/0186501 A1 | 8/2008 | Xie |
| 2008/0207996 A1 | 8/2008 | Tsai |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2008/0287795 A1* | 11/2008 | Klingensmith ....... G06T 7/0012 600/443 |
| 2009/0018565 A1 | 1/2009 | To et al. |
| 2009/0018566 A1 | 1/2009 | Escudero et al. |

(56) References Cited

U.S. PATENT DOCUMENTS

| | | |
|---|---|---|
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |
| 2009/0073444 A1 | 3/2009 | Wang |
| 2009/0073455 A1 | 3/2009 | Onimura |
| 2009/0076447 A1 | 3/2009 | Casas et al. |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196477 A1 | 8/2009 | Cense |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0234220 A1 | 9/2009 | Maschke |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0268159 A1 | 10/2009 | Xu et al. |
| 2009/0275966 A1 | 11/2009 | Mitusina |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1 | 4/2010 | Honeck et al. |
| 2010/0125253 A1 | 5/2010 | Olson |
| 2010/0130996 A1 | 5/2010 | Doud et al. |
| 2010/0198081 A1 | 8/2010 | Hanlin et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0004107 A1* | 1/2011 | Rosenthal .......... A61M 25/0074 600/479 |
| 2011/0023617 A1 | 2/2011 | Yo et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0137140 A1 | 6/2011 | Tearney et al. |
| 2011/0144673 A1 | 6/2011 | Zhang et al. |
| 2011/0201924 A1 | 8/2011 | Tearney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0123352 A1 | 5/2012 | Fruland et al. |
| 2012/0136350 A1 | 5/2012 | Goshgarian et al. |
| 2012/0203230 A1 | 8/2012 | Adams |
| 2012/0238869 A1 | 9/2012 | Schmitt et al. |
| 2012/0259337 A1 | 10/2012 | del Rio et al. |
| 2012/0277730 A1 | 11/2012 | Salahieh et al. |
| 2012/0289971 A1 | 11/2012 | Segermark et al. |
| 2013/0023865 A1 | 1/2013 | Steinke et al. |
| 2013/0035692 A1 | 2/2013 | Sorensen et al. |
| 2013/0072787 A1 | 3/2013 | Wallace et al. |
| 2013/0184549 A1 | 7/2013 | Avitall et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0287282 A1 | 10/2013 | Yokota et al. |
| 2013/0317519 A1 | 11/2013 | Romo et al. |
| 2013/0325003 A1 | 12/2013 | Kapur et al. |
| 2013/0331819 A1 | 12/2013 | Rosenman et al. |
| 2014/0005534 A1 | 1/2014 | He et al. |
| 2014/0046250 A1 | 2/2014 | Jain et al. |
| 2014/0128893 A1 | 5/2014 | Guggenheimer et al. |
| 2014/0187949 A1 | 7/2014 | Zhao et al. |
| 2014/0222042 A1 | 8/2014 | Kessler et al. |
| 2014/0222047 A1 | 8/2014 | Vreeman |
| 2014/0243881 A1 | 8/2014 | Lees et al. |
| 2014/0275996 A1 | 9/2014 | Stigall |
| 2014/0291985 A1 | 10/2014 | Cabrera et al. |
| 2014/0343410 A1 | 11/2014 | Graf et al. |
| 2014/0371718 A1 | 12/2014 | Alvarez et al. |
| 2015/0025310 A1 | 1/2015 | Everingham et al. |
| 2015/0036146 A1 | 2/2015 | Staloff |
| 2015/0141816 A1 | 5/2015 | Gupta et al. |
| 2015/0146211 A1 | 5/2015 | Bhagavatula et al. |
| 2015/0320975 A1 | 11/2015 | Simpson et al. |
| 2015/0327866 A1 | 11/2015 | Eckhouse et al. |
| 2016/0008025 A1 | 1/2016 | Gupta et al. |
| 2016/0038030 A1 | 2/2016 | Smith et al. |
| 2016/0144155 A1 | 5/2016 | Simpson et al. |
| 2016/0262839 A1 | 9/2016 | Spencer et al. |
| 2017/0238803 A1 | 8/2017 | Kankaria |
| 2017/0238808 A1 | 8/2017 | Simpson et al. |
| 2018/0042520 A1 | 2/2018 | Patel et al. |
| 2018/0207417 A1 | 7/2018 | Zung et al. |
| 2019/0021679 A1 | 1/2019 | Christensen |
| 2019/0021760 A1 | 1/2019 | Newhauser et al. |
| 2019/0029714 A1 | 1/2019 | Patel et al. |
| 2019/0110809 A1 | 4/2019 | Rosenthal et al. |
| 2019/0209206 A1 | 7/2019 | Patel et al. |
| 2019/0313941 A1 | 10/2019 | Radjabi |
| 2020/0029801 A1 | 1/2020 | Tachibana et al. |
| 2020/0060718 A1 | 2/2020 | Patel et al. |
| 2020/0069253 A1 | 3/2020 | Black et al. |
| 2020/0069327 A1 | 3/2020 | Patel et al. |
| 2020/0315654 A1 | 10/2020 | Patel et al. |
| 2020/0323553 A1 | 10/2020 | Fernandez et al. |
| 2021/0177262 A1 | 6/2021 | Spencer et al. |
| 2021/0345903 A1 | 11/2021 | Patel et al. |
| 2022/0039828 A1 | 2/2022 | Patel et al. |
| 2022/0168011 A1 | 6/2022 | Patel et al. |
| 2022/0273336 A1 | 9/2022 | Fernandez et al. |
| 2022/0273337 A1 | 9/2022 | Patel et al. |
| 2023/0225616 A1 | 7/2023 | Patel et al. |

FOREIGN PATENT DOCUMENTS

| | | |
|---|---|---|
| CN | 101601581 A | 12/2009 |
| CN | 103027727 A | 4/2013 |
| CN | 104968285 A | 10/2015 |
| DE | 202006018883.5 U | 2/2007 |
| EP | 0347098 A2 | 12/1989 |
| EP | 0808638 A1 | 11/1997 |
| EP | 0845692 B1 | 11/2005 |
| EP | 1859732 A1 | 11/2007 |
| EP | 2090245 A1 | 8/2009 |
| EP | 2353526 B1 | 9/2013 |
| EP | 2942028 A1 | 11/2015 |

(56) References Cited

FOREIGN PATENT DOCUMENTS

| | | |
|---|---|---|
| EP | 3446648 A1 | 2/2019 |
| JP | S62-275425 A | 11/1987 |
| JP | 03502060 A | 2/1990 |
| JP | H05501065 A | 3/1993 |
| JP | 05103763 A | 4/1993 |
| JP | 06027343 A | 2/1994 |
| JP | H07184888 A | 7/1995 |
| JP | 07308393 A | 11/1995 |
| JP | 2002214127 A | 7/2002 |
| JP | 2004509695 A | 4/2004 |
| JP | 2004516073 A | 6/2004 |
| JP | 2005114473 A | 4/2005 |
| JP | 2005230550 A | 9/2005 |
| JP | 2005249704 A | 9/2005 |
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |
| JP | 200783053 A | 4/2007 |
| JP | 200783057 A | 4/2007 |
| JP | 2007225349 A | 9/2007 |
| JP | 2007533361 A | 11/2007 |
| JP | 2008023627 | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |
| JP | 2009509690 A | 3/2009 |
| JP | 200978150 A | 4/2009 |
| JP | 2009066252 A | 4/2009 |
| JP | 2009201969 A | 9/2009 |
| JP | 2010042182 A | 2/2010 |
| JP | 2010518900 A | 6/2010 |
| JP | 2011521747 A | 7/2011 |
| JP | 2012143558 A | 8/2012 |
| JP | 2012229976 A | 11/2012 |
| JP | 2012533353 A | 12/2012 |
| JP | 2013512736 A | 4/2013 |
| JP | 2013/524930 A | 6/2013 |
| JP | 2015533584 A | 11/2015 |
| JP | 2016508758 A | 3/2016 |
| KR | 2007/0047221 A | 5/2007 |
| RU | 2185859 C2 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |
| WO | WO2008/065600 A2 | 6/2008 |
| WO | WO2008/086613 A1 | 7/2008 |
| WO | WO2008/087613 A2 | 7/2008 |
| WO | WO2008/151155 A2 | 12/2008 |
| WO | WO2009/005779 A1 | 1/2009 |
| WO | WO2009/006335 A1 | 1/2009 |
| WO | WO2009/009799 A1 | 1/2009 |
| WO | WO2009/009802 A1 | 1/2009 |
| WO | WO2009/023635 A1 | 2/2009 |
| WO | WO2009/024344 A1 | 2/2009 |
| WO | WO2009/094341 A2 | 7/2009 |
| WO | WO2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO2012/057940 A1 | 5/2012 |
| WO | WO2012/061935 A1 | 5/2012 |
| WO | WO2012/123737 A1 | 9/2012 |
| WO | WO2012/166332 A1 | 12/2012 |
| WO | WO2013/033490 A1 | 3/2013 |
| WO | WO2013/056262 A1 | 4/2013 |
| WO | WO2014/077870 A1 | 5/2014 |
| WO | WO2014/093148 A2 | 6/2014 |
| WO | WO2015/074018 A1 | 5/2015 |
| WO | WO2015/101747 A1 | 7/2015 |
| WO | WO2015/120146 A1 | 8/2015 |
| WO | WO2015/165736 A1 | 11/2015 |

OTHER PUBLICATIONS

Patel et al.; U.S. Appl. No. 17/455,655 entitled "Atherectomy catheter with shapeable distal tip," filed Nov. 18, 2021.

Aziz et al.; Chronic total occlusions - a stiff challenge requiring a major breakthrough: is there light at the end of the tunnel ?; Heart; vol. 91; suppl. III; pp. 42-48; Jun. 2005.

Bayer Material Science: : Snap-Fit Joints for Plastics; 26 pages; retrieved from the Internet: ( https://web.archive.org/web/20121119232733if_/http://fab.cba.mit.edu:80/classes/S62.12/people/vemnelle.noel/Plastic Snap_fit_design.pdf) on Sep. 26, 2018.

Cioppa et al.; Safety and efficacy of fernoro-popliteal chronic total occlusions recanalisation using the ocelot, oct-guided intraluminal crossing system. Single center experience; (Presentation abstract); ICCAD; 10th International Congress on Coronary Artery Disease; Florence, Italy; Published in Cardiology: 126, suppl. 2; p. 493; Oct. 13-16, 2013.

Choma et al.; Sensitivity advantage of swept source and fourier domain optical coherence tomography; Optics Express; 11(18); pp. 2183-2189; Sep. 8, 2003.

De Boer et al.; Improved signal-to-noise ratio in spectral-domain compared with time-domain optical coherence tomography; Optics Letters; 28(21); pp. 2067-2069; Nov. 2003.

Emkey et al.; Analysis and evaluation of graded-index fiber-lenses; Journal of Lightwave Technology; vol. LT-5; No. 9; pp. 1156-1164; Sep. 1987.

Golomb et al.; Contemporary reviews in cardiovascular medicine: peripheral arterial disease morbidity and mortality implications; Circulation; 114(7); pp. 688-699; Aug. 15, 2006.

Gonzalo et al.; Optical coherence tomography patterns of stent restenosis; Am. Heart J .; 158(2); pp. 284-293; Aug. 2009.

Han et al.; In situ Frog Retina Imaging Using Common-Path OCT with a Gold-Coated Bare Fiber Probe; CFM6; San Jose, California; CLEO, May 4, 2008; 2 pages.

Krishnan et al.; Histopathologic evidence of adventitial cuts predicts retenosis after directional atherectomy of lower extremity peripheral arterial disease: results from a randomized, open label, investigator-initiated trial comparing intravascular ultrasound-guided atherectomy to angiography guided atherectomy in peripheral vascular interventions for TASC's A, B lesions (utopia) pilot study; Journal of the American College of Cardiology; 59(13); p. E2083; Mar. 27, 2012.

Leitgeb et al.; Performance of fourier domain vs time domain optical coherence tomography; Optics Express; 11(8); pp. 889-894; Apr. 21, 2003.

Linares et al.; Arbitrary single-mode coupling by tapered and nontapered grin fiber lenses; Applied Optics; vol. 29; No. 28; pp. 4003-4007; Oct. 1, 1990.

Muller et al.; Time-gated infrared fourier-domain optical coherence tomography; CFM5; San Jose, California; CLEO May 4, 2008; 2 pages.

Rogers et al.; The right to bear legs-an amendment to healthcare: how preventing amputations can save billions for the US health-care system; Journal of American Podiatric Medical Association; 98(2); pp. 166-168; Mar./Apr. 2008.

Rollins et al.; Optimal interferometer designs for optical coherence tomography; Optics Letters; 24(21); pp. 1484-1486; Nov. 1999.

Schmitt et al.; A new rotational thrombectomy catheter: System design and first clinical experiences; Cardiovascular and Interventional Radiology; Springer-Verlag; 22(6); pp. 504-509; Nov. 1, 1999.

(56) References Cited

OTHER PUBLICATIONS

Sharma et al.; Common-path optical coherence tomography with side-viewing bare fiber probe for endoscopic optical coherence tomography; Rev. Sci. Instrum.; vol. 78; 113102; 5 pages; Nov. 6, 2007.
Sharma et al.; Optical coherence tomography based on an all-fiber autocorrelator using probe-end reflection as reference; CWJ13; San Francisco, California; CLEO May 16, 2004; 4 pages.
Shinkle et al.; Evaluation of stent placement and outcomes with optical coherence tomography; Interv. Cardiol.; 2(4); pp. 535-543; (manuscript version, 12 pages); Aug. 2010.
Smith et al.; Re-entry devices in the treatment of peripheral chronic occlusion; Texas Heart Institute J.; 38(4); pp. 392-397; Aug. 2011.
Stamper et al.; Plaque characterization with optical coherence tomography. Journal of the American College of Cardiology. 47(8); pp. 69-79; Apr. 18, 2006.
Suparno et al.; Light scattering with single-mode fiber collimators; Applied Optics; vol. 33; No. 30; pp. 7200-7205; Oct. 20, 1994.
Tanaka et al.; Challenges on the frontier of intracoronary imaging. atherosclerotic plaque macrophage measurement by optical coherence tomography; Journal of Biomedical Optics; 15(1); pp. (011104-1)-(011104-8); Jan.-Feb. 2010.
Taylor et al.; An all inclusive and transparent view of a vascular program's direct impact on its health system; J. Vasc. Surg.; 55(1); pp. 281-285; Jan. 2012.
Tentolouris et al; Mortality in diabetic and nondiabetic patients after amputations performed from 1990 to 1995: a 5 year follow-up study; Diabetes Care; 27(7); pp. 1598-1604; Jul. 2004.
Wang et al.; Common-path endoscopic Fourier domain OCT with a reference Michelson interferometer; Proceedings of the SPIE; vol. 7566; pp. 75660L-75660L-7; Jan. 2010.
Patel et al.; U.S. Appl. No. 16/801,047 entitled "Micro-molded anamorphic reflector lens for image guided therapeutic/diagnostic catheters," filed Feb. 25, 2020.
Smith et al.; U.S. Appl. No. 16/941,310 entitled "Chronic total occlusion crossing devices with imaging," filed Jul. 28, 2020.
Spencer et al.; U.S. Appl. No. 16/943,446 entitled "Catheter-based off-axis optical coherence tomography imaging system," filed Jul. 30, 2020.
Patel et al.; U.S. Appl. No. 17/046,066 entitled "Occlusion-crossing devices," filed Oct. 8, 2020.
Tachibana et al.; U.S. Appl. No. 17/645,722 entitled "Atherectomy catheter drive assemblies," filed Dec. 22, 2021.
Black et al.; U.S. Appl. No. 17/652,073 entitled "Optical coherence tomography for biological imaging," filed Feb. 22, 2022.
Patel et al.; U.S. Appl. No. 17/762,815 entitled "Atherectomy catheter with shapeable distal tip," filed Mar. 23, 2022.
Patel et al.; U.S. Appl. No. 17/763,810 entitled "Occlusion-crossing devices," filed Mar. 25, 2022.
Patel et al.; U.S. Appl. No. 17/347,419 entitled "Micro-molded anamorphic reflector lens for image guided therapeutic/diagnostic catheters," filed Jun. 14, 2021.
Gupta et al.; U.S. Appl. No. 17/445,648 entitled "Tissue collection device for catheter," filed Aug. 23, 2021.
Simpson et al.; U.S. Appl. No. 17/449,867 entitled "Occlusion-crossing devices, imaging, and atherectomy devices," filed Oct. 4, 2021.
Spencer et al.; U.S. Appl. No. 17/449,895 entitled "Occlusion-crossing devices, atherectomy devices, and imaging," filed Oct. 4, 2021.
Merriam Webster; Proximal (Definition); 10 pages; retrieved from the internet (https://www.merriam-webster.com/dictionary/proximal) on Jun. 9, 2021.
Wikipedia; Hinge; 4 pages; retrieved from the internet (https://en.wikipedia.org/w/index.php?title=Hinge&oldid=479569345) on Jun. 9, 2021.
Smith et al.; U.S. Appl. No. 17/189,123 entitled "Optical pressure sensor assembly," filed Mar. 1, 2021.
Kankaria; U.S. Appl. No. 17/209,162 entitled "Optical coherence tomography with graded index fiber for biological imaging," filed Mar. 22, 2021.
Newhauser et al.; U.S. Appl. No. 17/209,168 entitled "Occlusion-crossing devices," filed Mar. 22, 2021.

\* cited by examiner

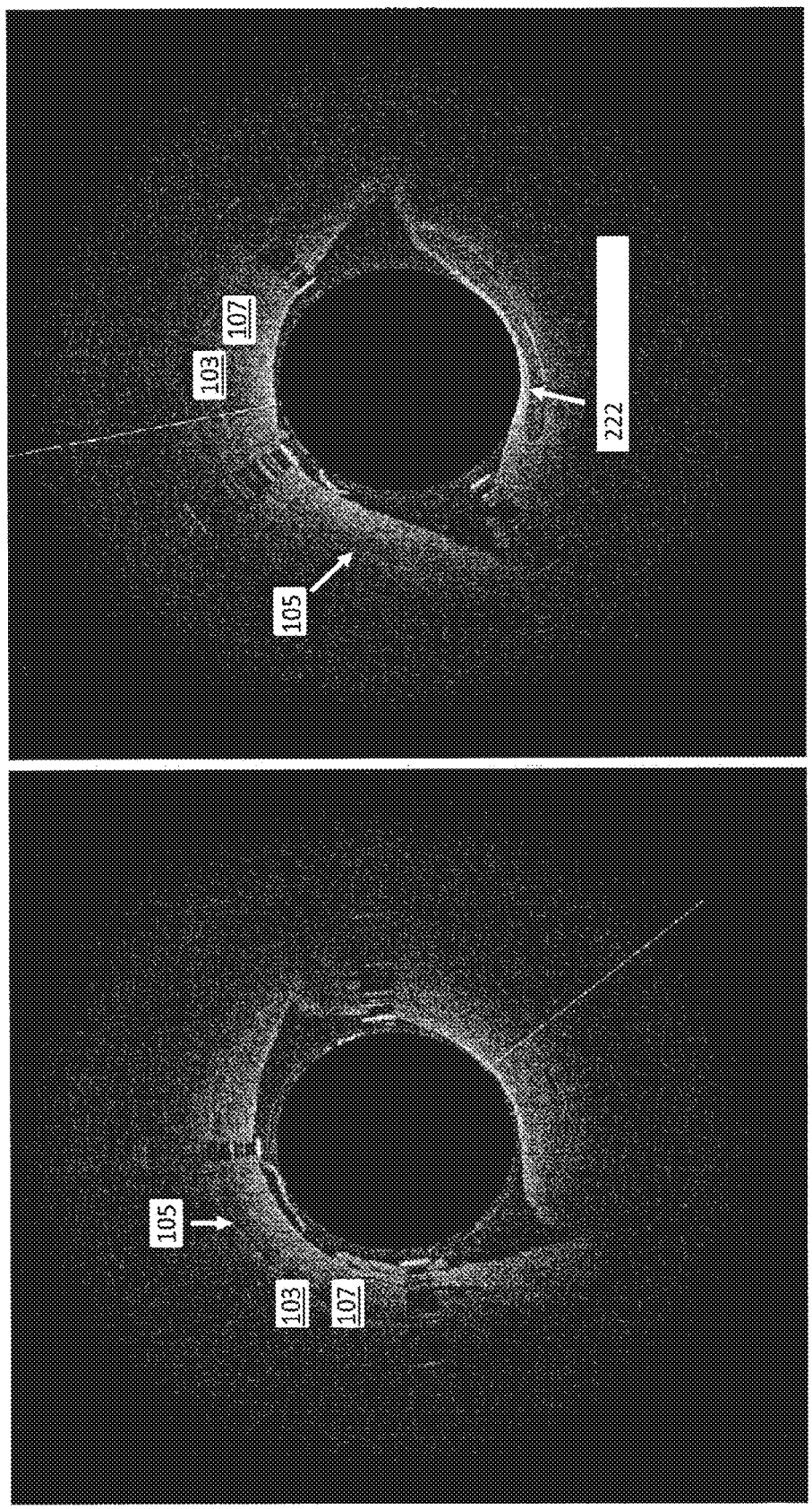

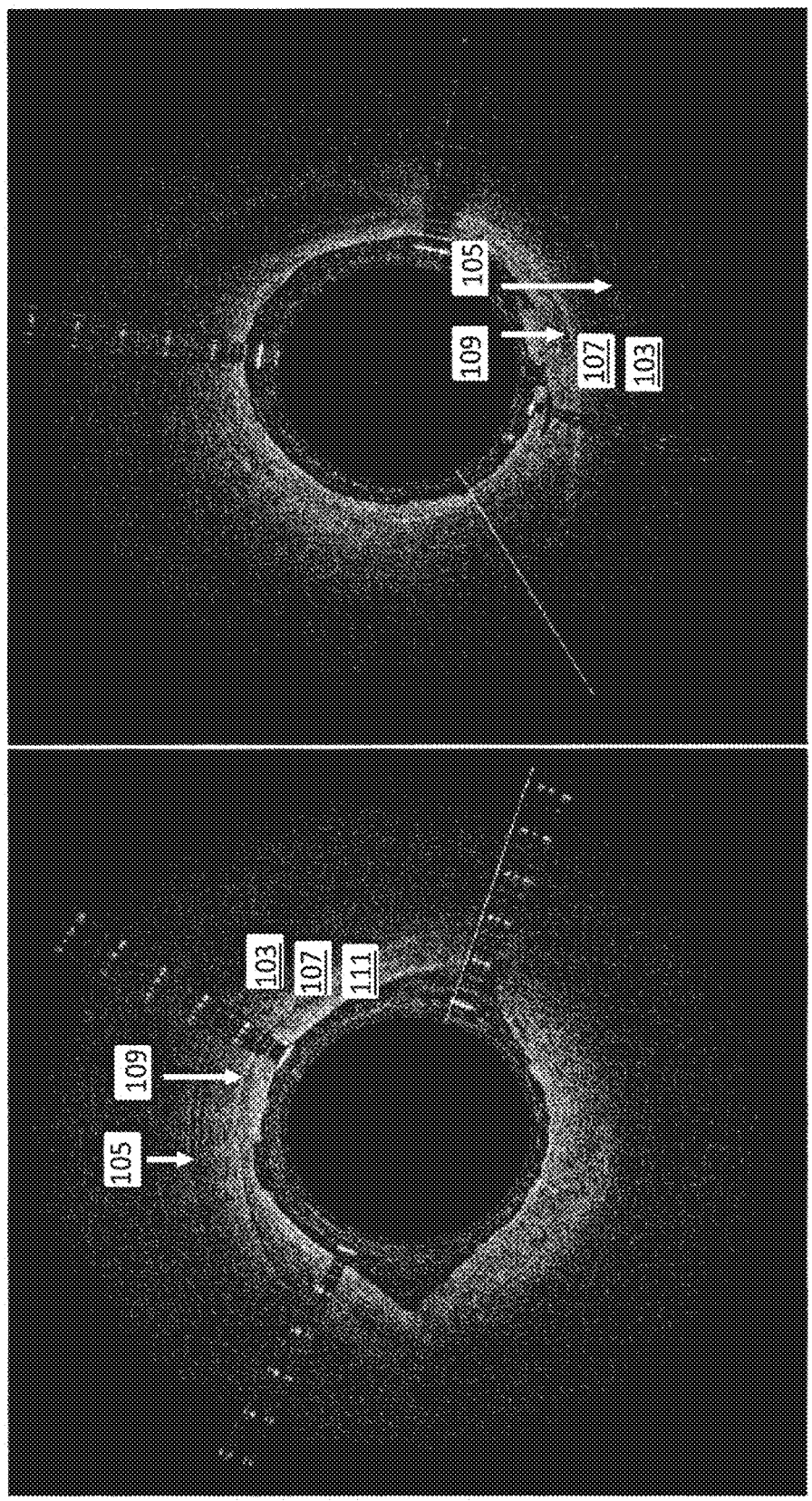

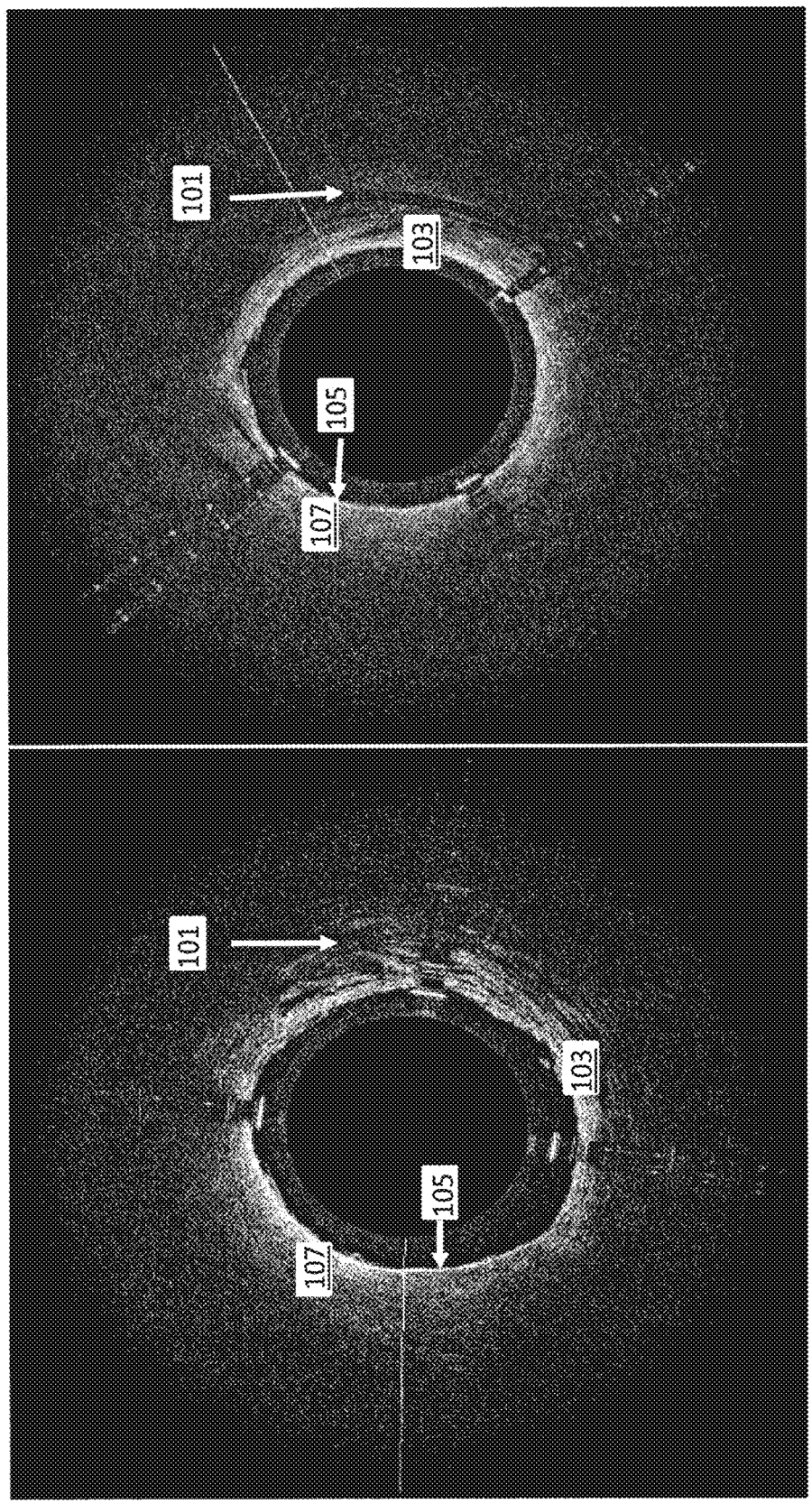

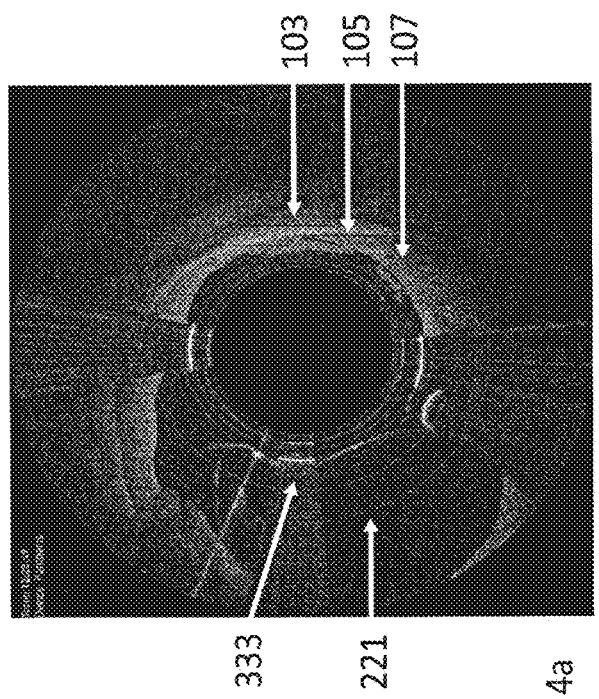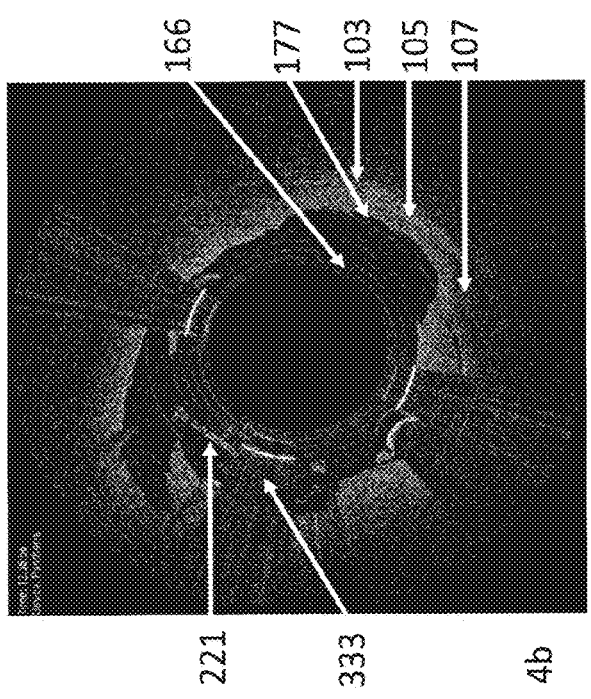
Figure 4a
Figure 4b

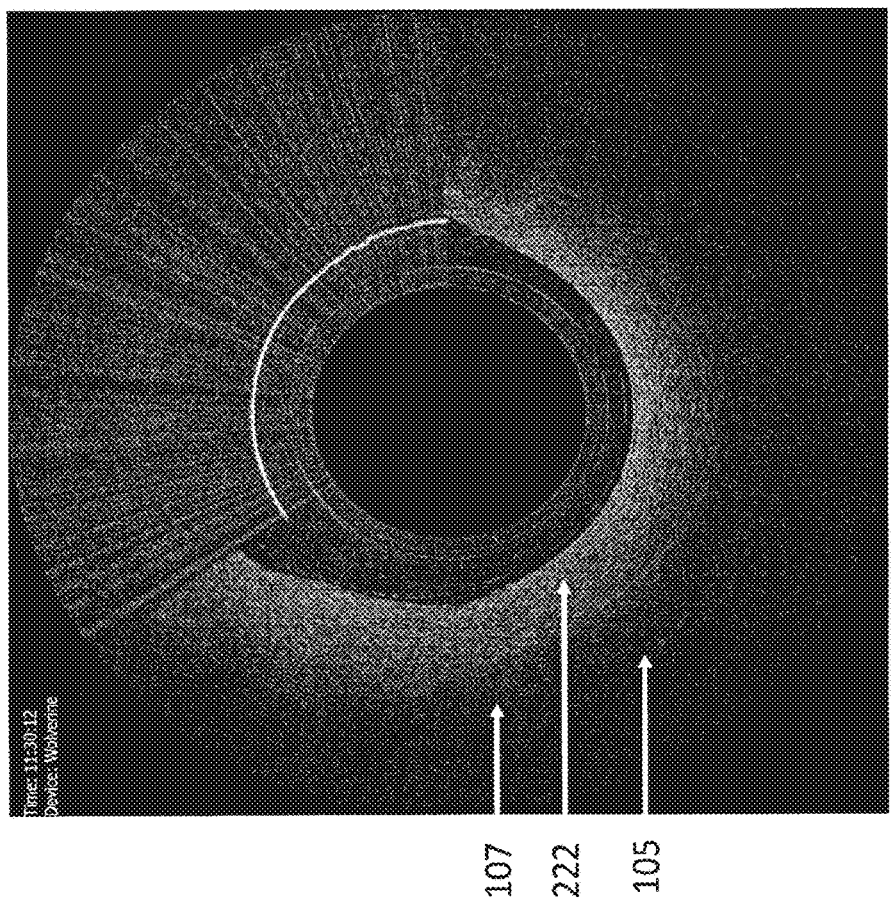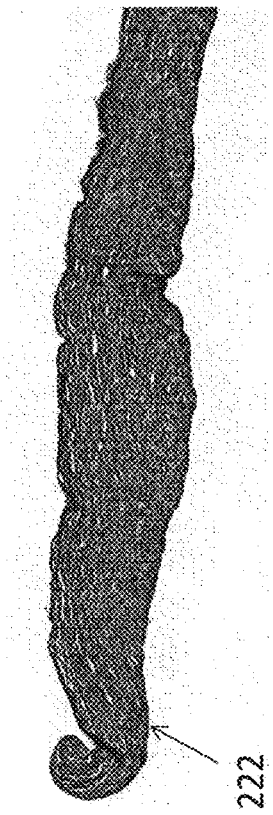
Figure 6a

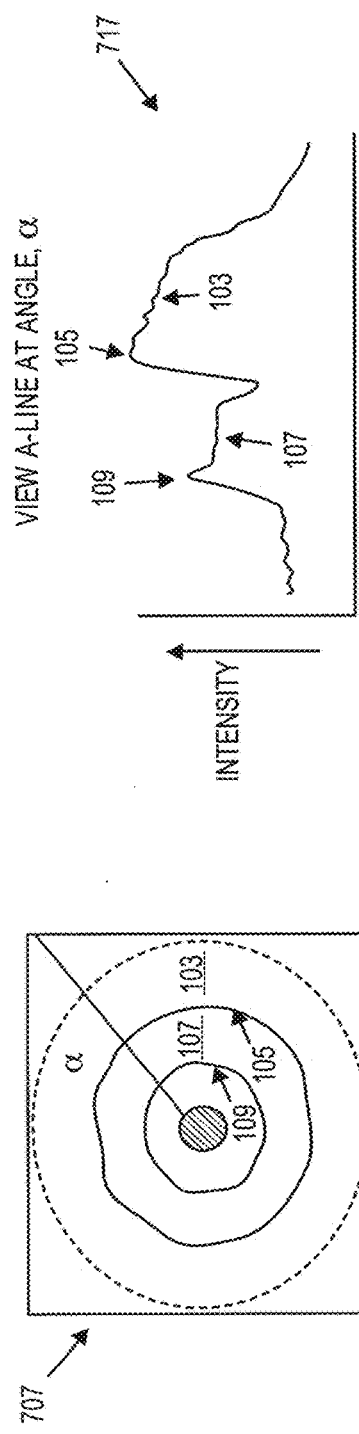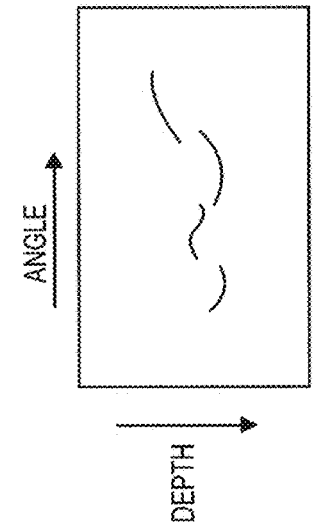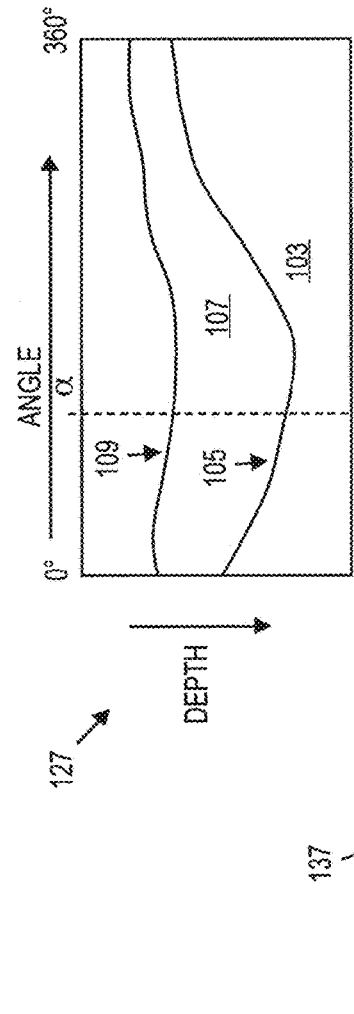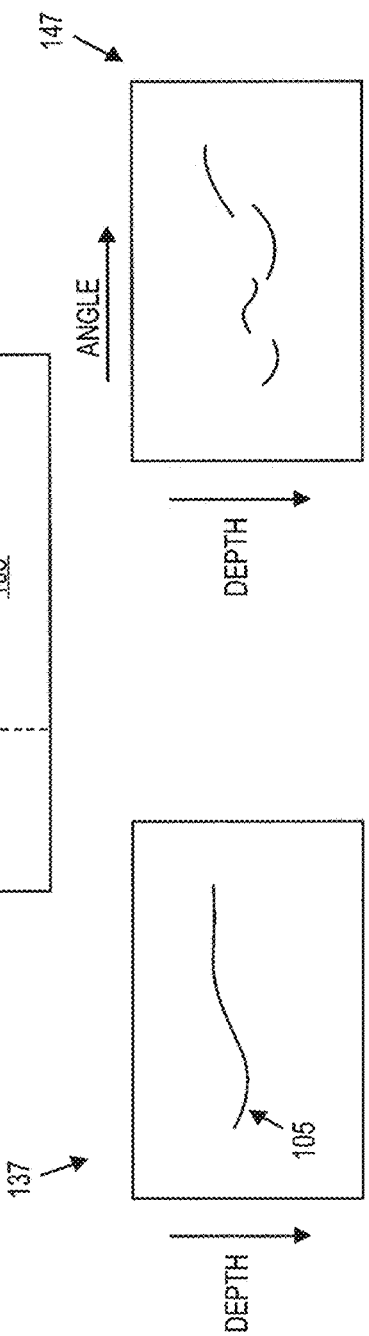

IDENTIFICATION OF ELASTIC LAMINA TO GUIDE INTERVENTIONAL THERAPY

CROSS REFERENCE TO RELATED APPLICATIONS

This application is a continuation of U.S. patent application Ser. No. 16/194,183, filed on Nov. 16, 2018, titled "IDENTIFICATION OF ELASTIC LAMINA TO GUIDE INTERVENTIONAL THERAPY," now U.S. Publication No. US-2019-0159796-A1, which is a continuation of U.S. patent application Ser. No. 14/899,893, filed on Dec. 18, 2015, titled "IDENTIFICATION OF ELASTIC LAMINA TO GUIDE INTERVENTIONAL THERAPY," now U.S. Pat. No. 10,130,386, which is a 371 of International Patent Application No. PCT/US2014/045799, filed on Jul. 8, 2014, titled "IDENTIFICATION OF ELASTIC LAMINA TO GUIDE INTERVENTIONAL THERAPY," now International Publication No. WO 2015/006353, which claims priority to U.S. Provisional Patent Application No. 61/843,866, titled "IDENTIFICATION OF ELASTIC LAMINA TO GUIDE INTERVENTIONAL THERAPY," filed on Jul. 8, 2013, each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Referring to FIG. 1, a normal healthy artery wall includes layers of tissue, such as the innermost intima 111, the media 107, the adventitia 103, and the periadventitia 101. The intima 111, media 107, and adventitia 103 are separated by two elastic membranes. The inner membrane is the internal elastic lamina (IEL) 109, which separates the intima 111 from the media 107, and the outer membrane is the external elastic lamina (EEL) 105, which separates the media 107 from the adventitia 103.

Coronary artery disease (CAD) and Peripheral artery disease (PAD) are both caused by the progressive narrowing of the blood vessels most often caused by atherosclerosis, the collection of plaque or a fatty substance along the inner lining or intima of the artery wall. Over time, this substance hardens and thickens, which can cause an occlusion in the artery, completely or partially restricting flow through the artery. Blood circulation to the arms, legs, stomach and kidneys brain and heart may be reduced, increasing the risk for stroke and heart disease.

Peripheral artery disease (PAD) and coronary artery disease (CAD) affect millions of people in the United States alone. PAD and CAD are silent, dangerous diseases that can have catastrophic consequences when left untreated. CAD is the leading cause of death in the United States while PAD is the leading cause of amputation in patients over 50 and is responsible for approximately 160,000 amputations in the United States each year.

Interventional treatments for CAD and PAD may include endarterectomy and/or atherectomy. Endarterectomy is surgical removal of plaque from the blocked artery to restore or improve blood flow. Endovascular therapies such as atherectomy are typically minimally invasive techniques that open or widen arteries that have become narrowed or blocked. Other treatments may include angioplasty to open the artery. For example, a balloon angioplasty typically involves insertion of a catheter into a leg or arm artery and positioning the catheter such that the balloon resides within the blockage. The balloon, connected to the catheter, is expanded to open the artery. Surgeons may then place a wire mesh tube, called a stent, at the area of blockage to keep the artery open.

During interventional treatments, trauma often occurs to the IEL 109, media 107, EEL 105, and adventitia 103. Trauma to the EEL 105 and/or adventitia 103 can initiate a severe inflammatory response, which can accelerate scarring and cause potential closure of the vessel. Disruption of the EEL 105 can also signal complimentary and inflammatory factors that accelerate and further promote restenosis. Accordingly, an interventional treatment that avoids trauma to EEL 105, and thus to the adventitia 103, is desired.

SUMMARY OF THE DISCLOSURE

Described herein is a system and method for identifying elastic lamina during interventional procedures and treatments. Such identification can be used to avoid trauma to the external elastic lamina during such procedures and treatments.

In general, in one embodiment, a method of performing atherectomy includes: (1) inserting an atherectomy device into a vessel; (2) gathering optical coherence tomography (OCT) images using an imaging sensor on the device; (3) identifying an external elastic lamina in the OCT images; and (4) cutting tissue in the vessel based upon the identification.

This and other embodiments can include one or more of the following features. The OCT images can be a toroidal view of the vessel. Identifying an external elastic lamina can include identifying an outer-most bright line in the toroidal view. Cutting tissue in the vessel based upon the identification can include adjusting a depth of cut based upon the identification. Cutting tissue in the vessel based upon the identification can include reorienting a distal tip of the device based upon the identification. Cutting tissue in the vessel can include cutting right up to the external elastic lamina, but not through the external elastic lamina. The identification can be performed automatically. Adjusting the depth of cut can include moving the cutter from an active mode to a passive mode. Moving the cutter from an active mode to a passive mode can include at least partially deflating a balloon on the device. The adjusting step can be performed automatically. The reorienting step can include using a marker in the OCT images to reorient the tip. The method can further include determining a distance between the cutter and the external elastic lamina. The method can further include activating an alarm if the distance is below a threshold value. The method can further include stopping the cutting if the distance is below a threshold value. The method can further including highlighting the external lamina in the OCT images after the identifying step.

In general, in one embodiment, an atherectomy system includes a catheter having an OCT imaging sensor attached thereto configured to gather OCT images and a controller. The controller is configured to automatically identify an external elastic lamina in the OCT images.

This and other embodiments can include one or more of the following features. The system can further include a display connected to the controller, and the display can be configured to display the OCT images as a toroidal view of the vessel. The controller can be further configured to highlight the external elastic lamina in the OCT images on the display after identification. The controller can be further configured to adjust a depth of cut based upon the identification. Adjusting a depth of cut can include moving the cutter from an active mode to a passive mode. Moving the cutter from an active mode to a passive mode can include at least partially deflating a balloon on the device. The controller can be further configured to reorient a distal tip of the device based upon the identification. The controller can be further configured to determine a distance between the cutter and the external elastic lamina. The controller can be configured to activate an alarm if the distance is below a threshold value. The controller can be configured to prevent cutting if the distance is below a threshold value.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4a and 4b are OCT images taken with an imaging atherectomy device having an inflatable balloon to urge the cutter against the wall. FIG. 4a shows an OCT image during cutting into the media, close to the EEL and adventitia with the balloon fully inflated. FIG. 4B shown an OCT image where the balloon has been deflated to reduce the cutting depth and avoid the EEL and adventitia.

FIG. 5a shows the direction of cut directly towards the artery wall structure with media and EEL. FIG. 5b shows adjustment of the direction away from the artery wall and towards plaque.

FIGS. 6a-6h show exemplary tissue excised with the identification methods described herein and the OCT images taken during cutting procedures.

FIGS. 7a-7e show a method of automatic detection of the EEL with a controller.

DETAILED DESCRIPTION

Described herein is a system and method for identifying elastic lamina during interventional treatments using a catheter having on-board imaging.

Figure 1:
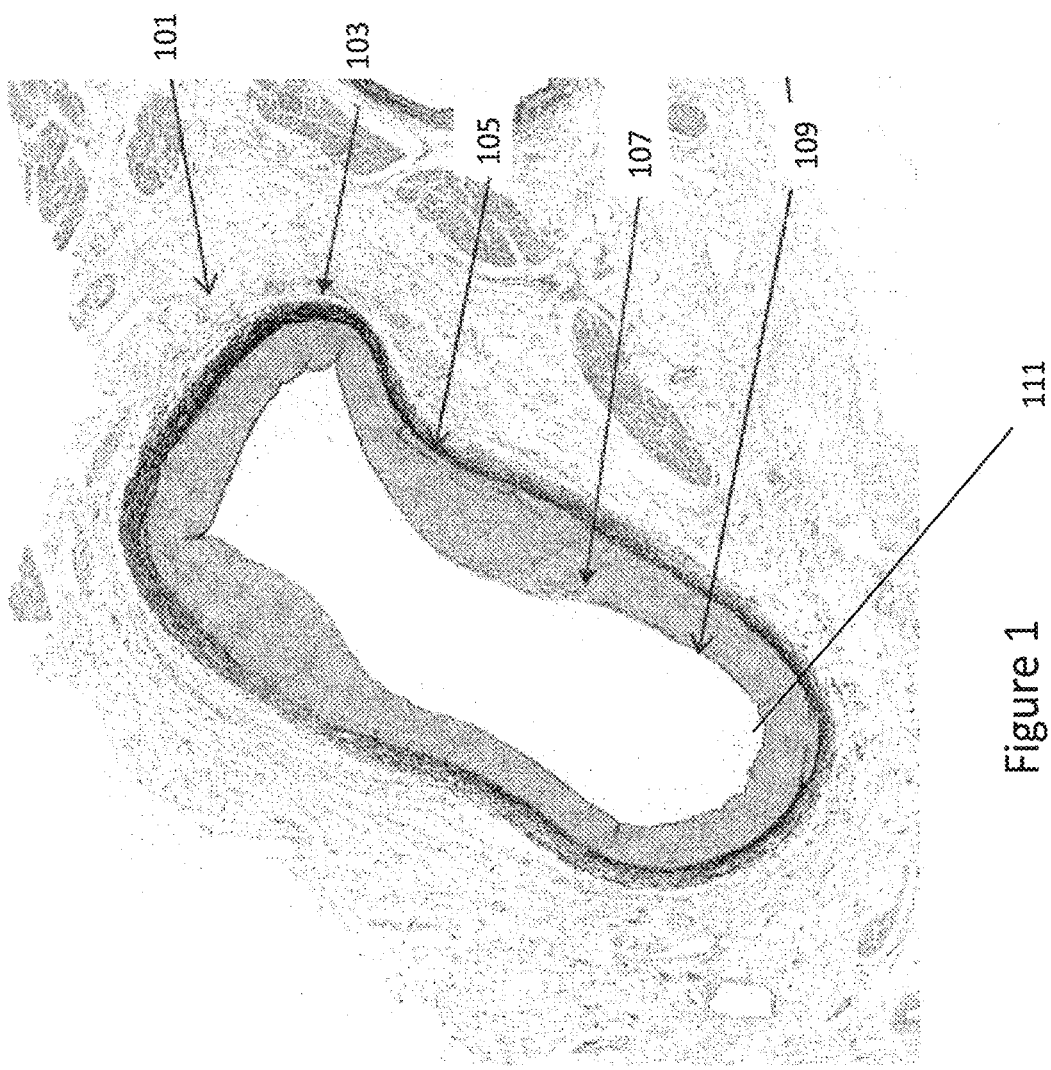
FIG. 1 is a histological view of a healthy vessel.
Figure 2:
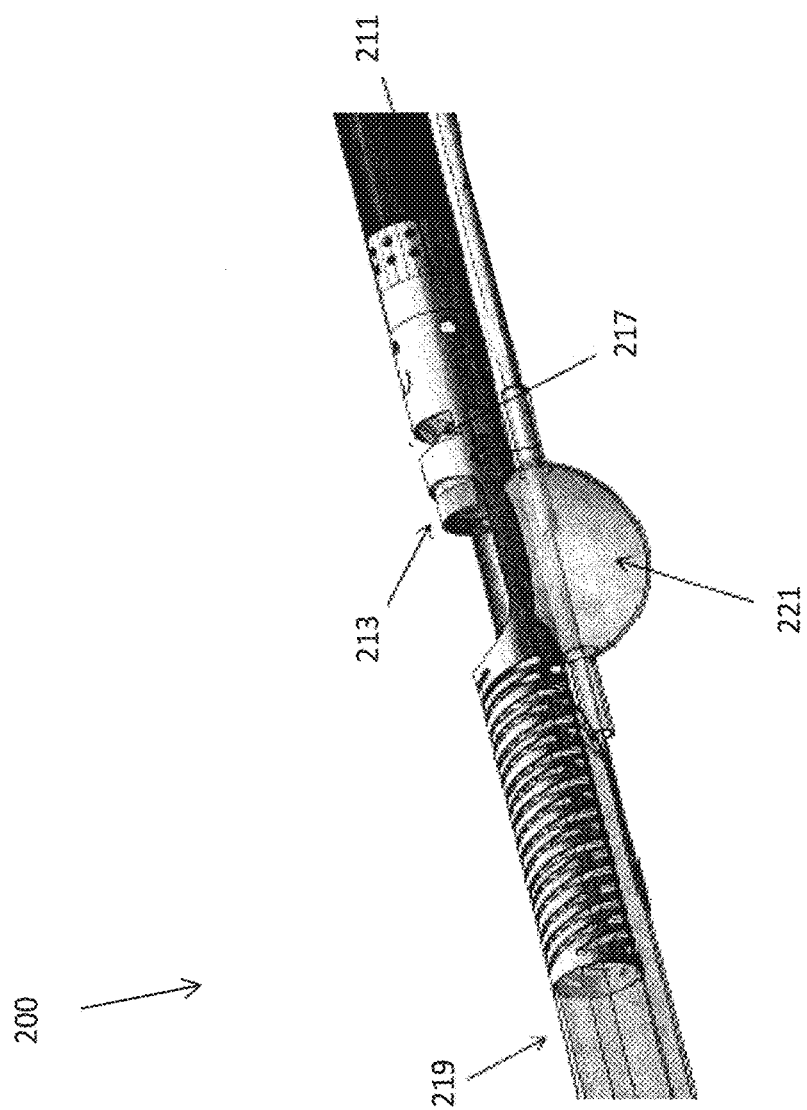
FIG. 2 is a view of an exemplary catheter with on-board imaging.

Referring to FIG. 2, an interventional catheter 200, such as an atherectomy catheter or an occlusion-crossing catheter, can include an elongate body 211 with a cutter 213 extending therefrom. An imaging sensor 217 can be configured to gather optical coherence tomography (OCT) images. A distal nosecone 219 can be configured to collect tissue cut by the cutter 213. In some embodiments, the device 200 can be a directional atherectomy device, and a balloon 221 can be used to expose the cutter 213 and/or urge the cutter 213 against the vessel wall for cutting. The amount of inflation of the balloon 212 can be varied to modify a depth of cut made by the cutter 213 into the vessel wall. Exemplary atherectomy devices are described further in U.S. patent application Ser. No. 12/829,277, filed Jul. 1, 2010, titled "ATHERECTOMY CATHETER WITH LATERALLY-DISPLACEABLE TIP," now U.S. Patent Application Publication No. 2011/0004107, U.S. patent application Ser. No. 13/175,232, filed Jul. 1, 2011, titled "ATHERECTOMY CATHETERS WITH LONGITUDINALLY DISPLACEABLE DRIVE SHAFTS," now U.S. Patent Application Publication No. 2012/0046679, U.S. patent application Ser. No. 13/654,357, filed Oct. 17, 2012, titled "ATHERECTOMY CATHETERS AND NON-CONTACT ACTUATION MECHANISM FOR CATHETERS," now U.S. Patent Application Publication No. 2013/0096589, International Patent Application No. PCT/US2013/031901, filed Mar. 15, 2013, titled "ATHERECTOMY CATHETERS WITH IMAGING," now published as WO 2013/172970, and International Patent Application No. PCT/US2013/032494, filed March 2013, titled "BALLOON ATHERECTOMY CATHETERS WITH IMAGING," now published as WO 2014/039099, the entireties of which are incorporated by reference herein.

Referring to FIGS. 3a-3ii, OCT images obtained with such an on-board imaging catheter can show the walls of the vessel, such as in a toroidal view of the walls. The resulting images can, for example, show plaque or thrombosis as well as layers of the vessel, including the backscattering or signal-rich intima 111, the media 107 that frequently has low backscattering or is signal-poor, the heterogeneous and frequently high backscattering adventitia 103, and/or the periadventitial tissue 101 characterized by large clear structures. The OCT image can further advantageously clearly show the IEL 109 as a distinct line between the media 107 and the intima 111 and the EEL 105 as a distinct line between the media 107 and the adventitia 103. For example, the IEL 109 and EEL 105 can be displayed as thin bright structures (i.e., be highly backscattering). In many cases, the IEL 109 and EEL 105 appear as continuous lines following along (substantially parallel with) the internal and external perimeter of the media 107.

The OCT images collected with the catheter can thus be used to clearly identify the EEL 105. Moreover, OCT advantageously has a higher resolution than other types of imaging, such as ultrasound, thereby allowing for the clear identification of the EEL 105. Further, upon identification the EEL 105 in the images, the interventional therapy (e.g., atherectomy) can be tailored so as to avoid or limit interaction with the EEL 105 and adventitia 103, thereby avoiding the inflammatory response that occurs if the EEL 105 or adventitia 103 are injured.

Referring to FIGS. 4a and 4b, in one embodiment, the depth of cut with the atherectomy catheter can be adjusted based upon the identification of the EEL 105, such as by deflating a balloon or otherwise adjusting the cutting depth, in order to avoid excising the EEL 105 or the adventitia 103. For example, FIG. 4a shows an OCT image where the balloon 221 is fully inflated. The resulting cut (the cutter position is indicated by the dark circle in the center and the direction is opposite to the middle marker 333) is close to the media 107 and EEL 105. In contrast, in FIG. 4b, the balloon 221 has been deflated in order to pull the cutter away and leave a space 166 between the cutter and the EEL 105 (note that FIG. 4b shows the cutting mark 177, close to the EEL 105, created by the cut of FIG. 4a).

Figure 5A:
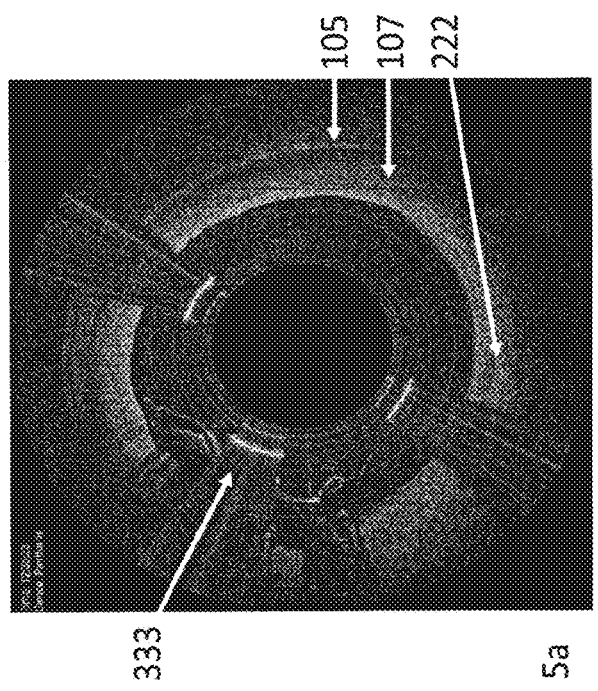
FIGS. 5a and 5b are OCT images taken with a directional atherectomy device.
Figure 5B:
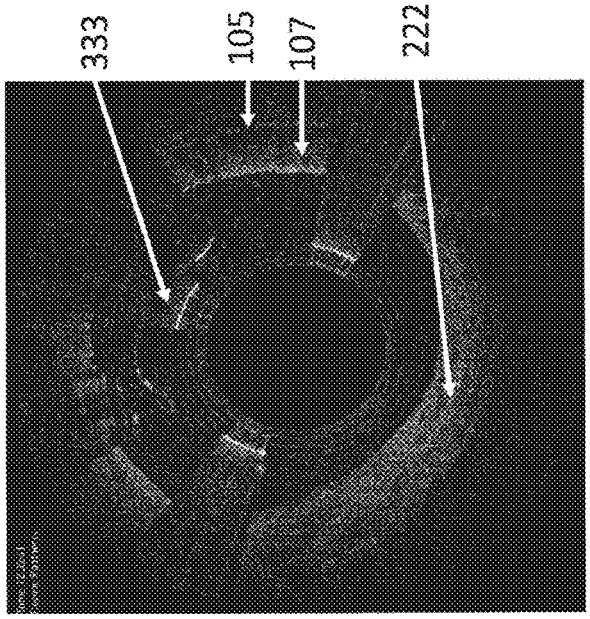
Figure 6B:
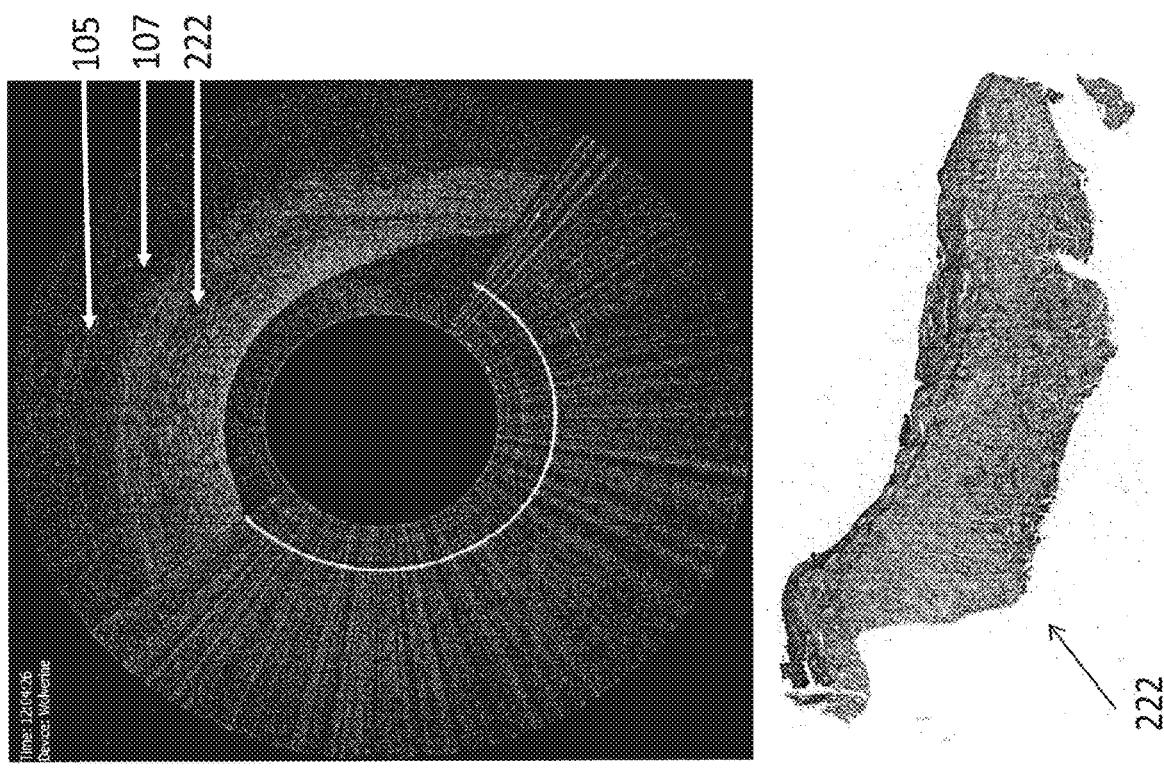
Figure 6C:
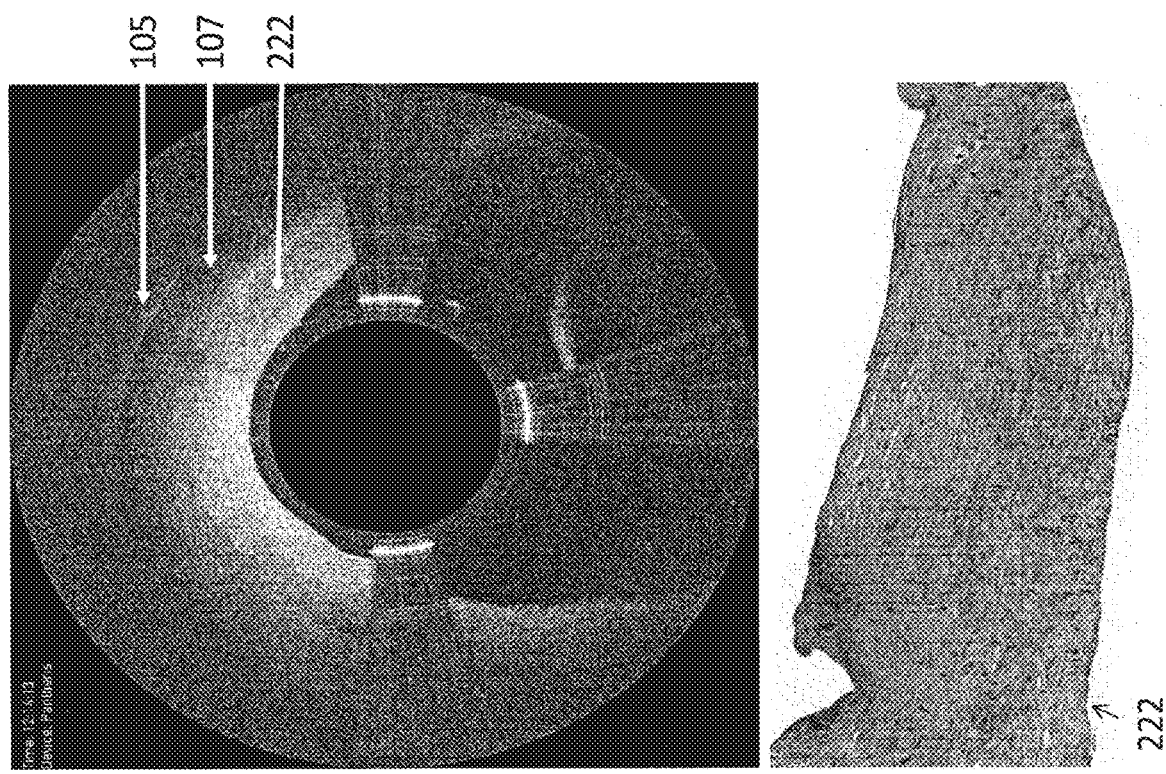
Figure 6D:
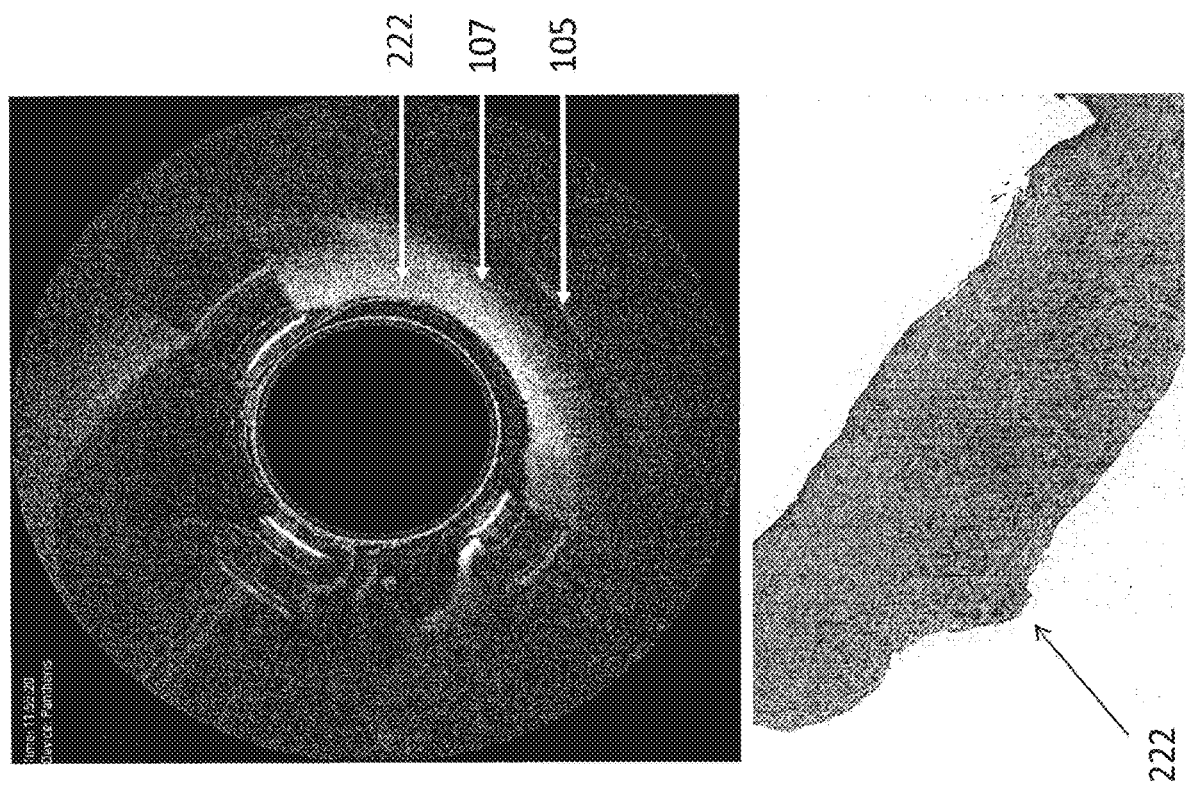
Figure 6E:
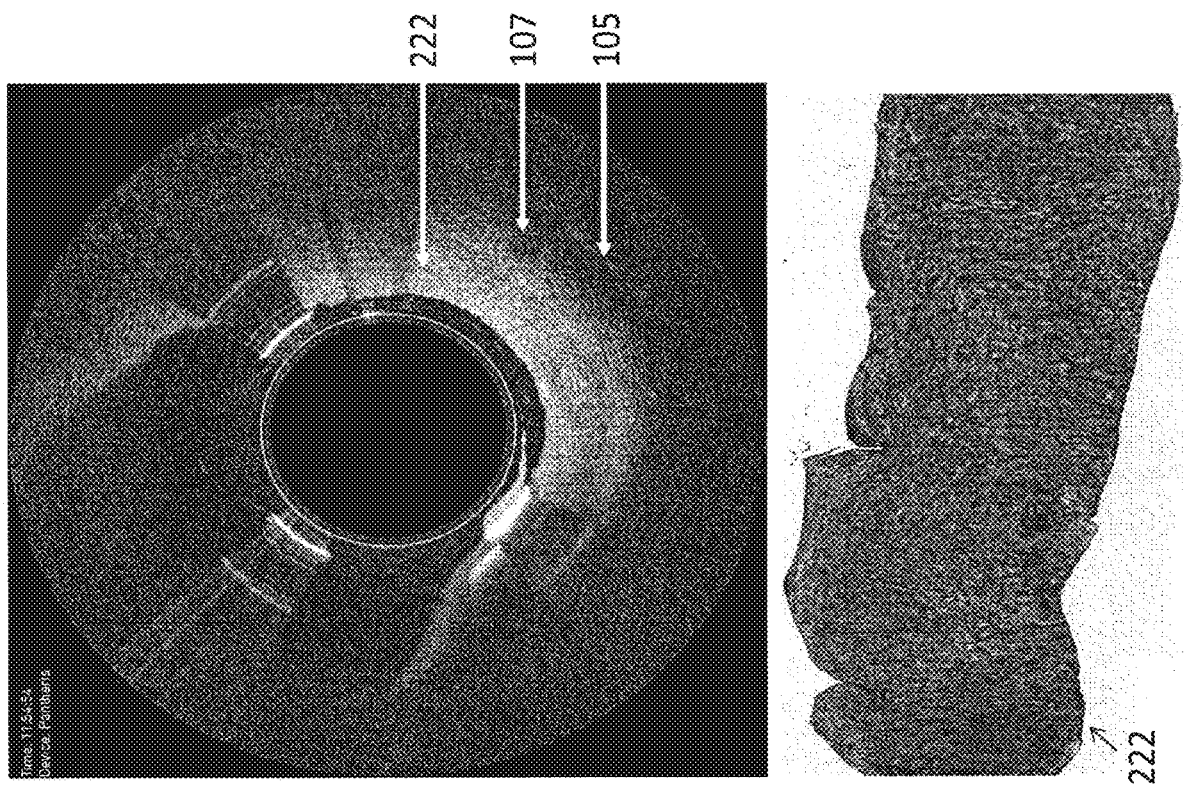
Figure 6F:
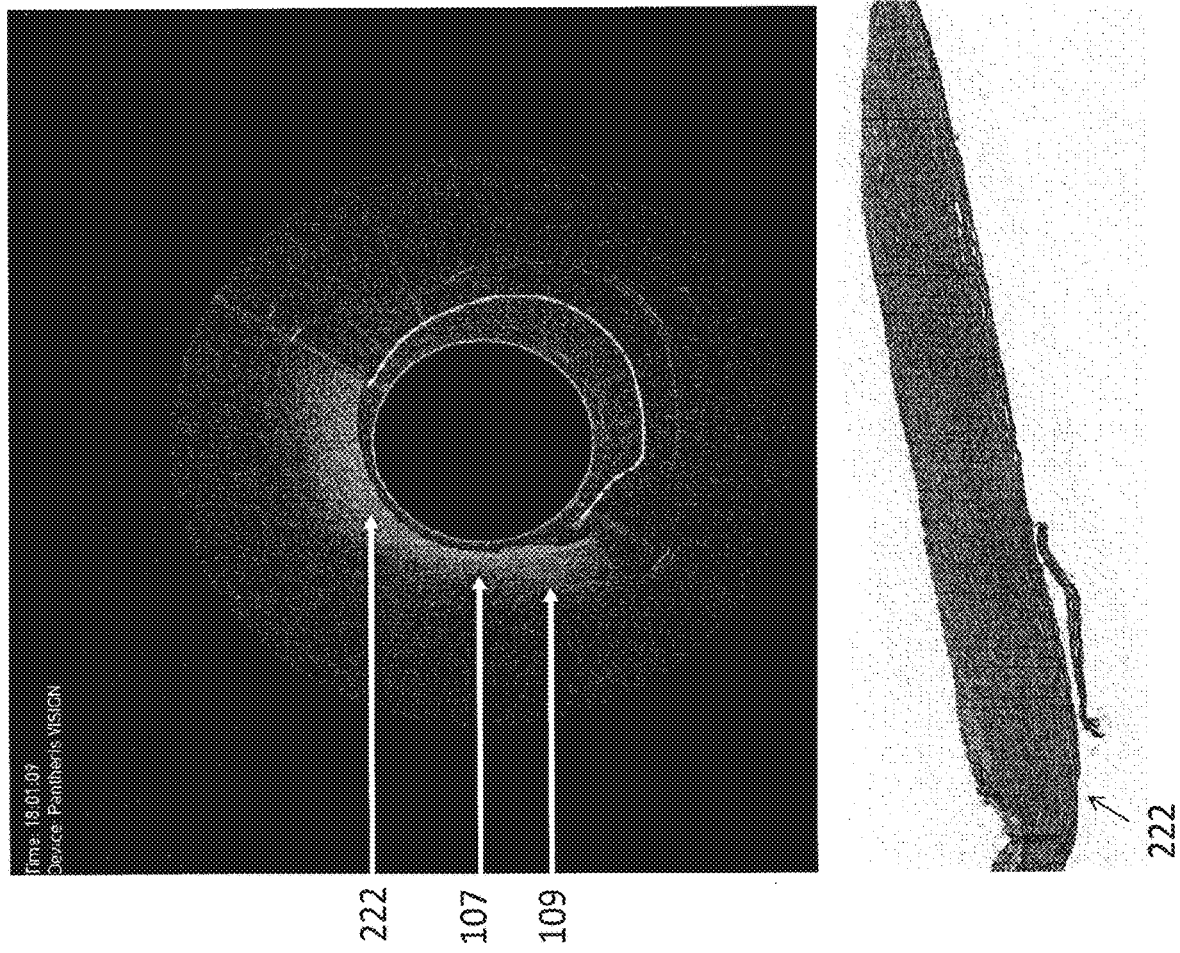
Figure 6G:
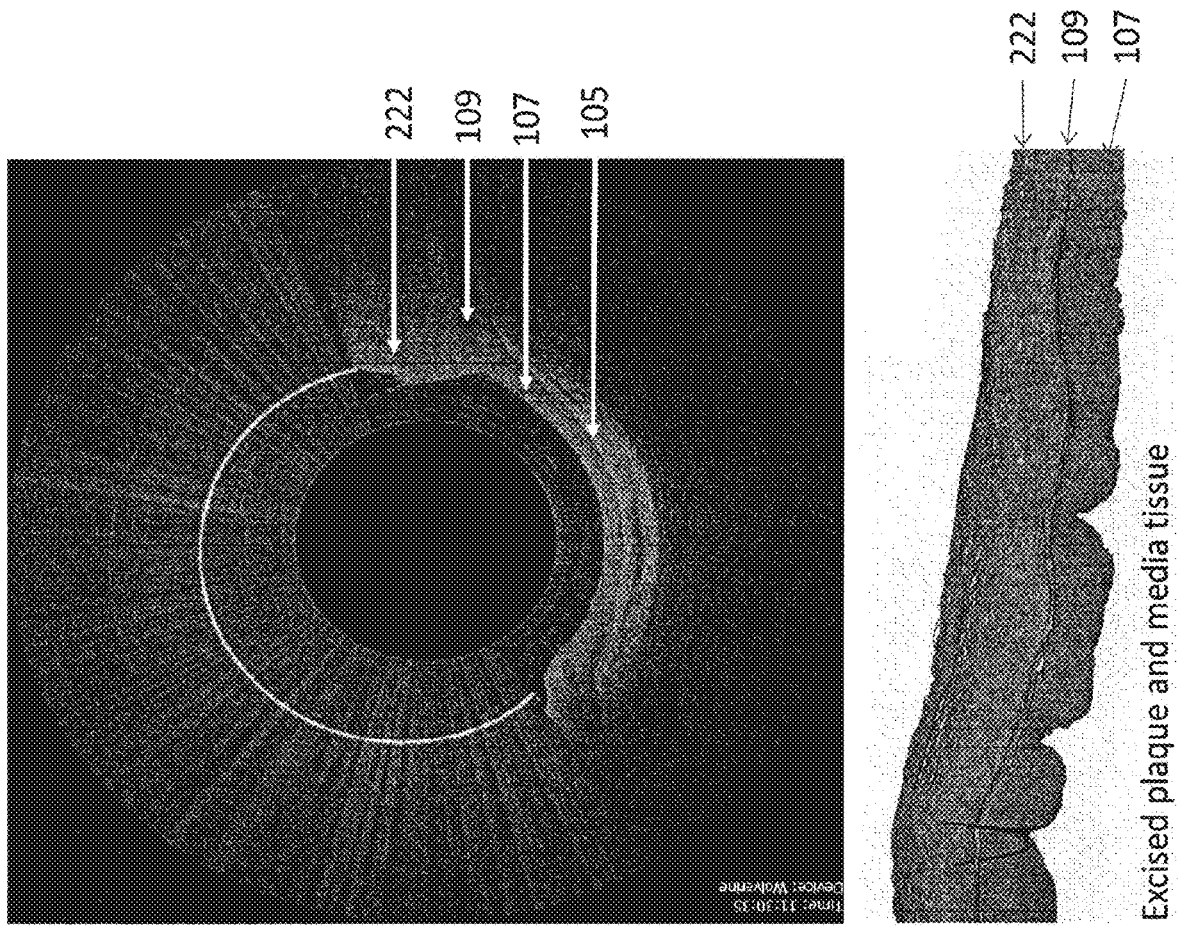
Figure 6H:
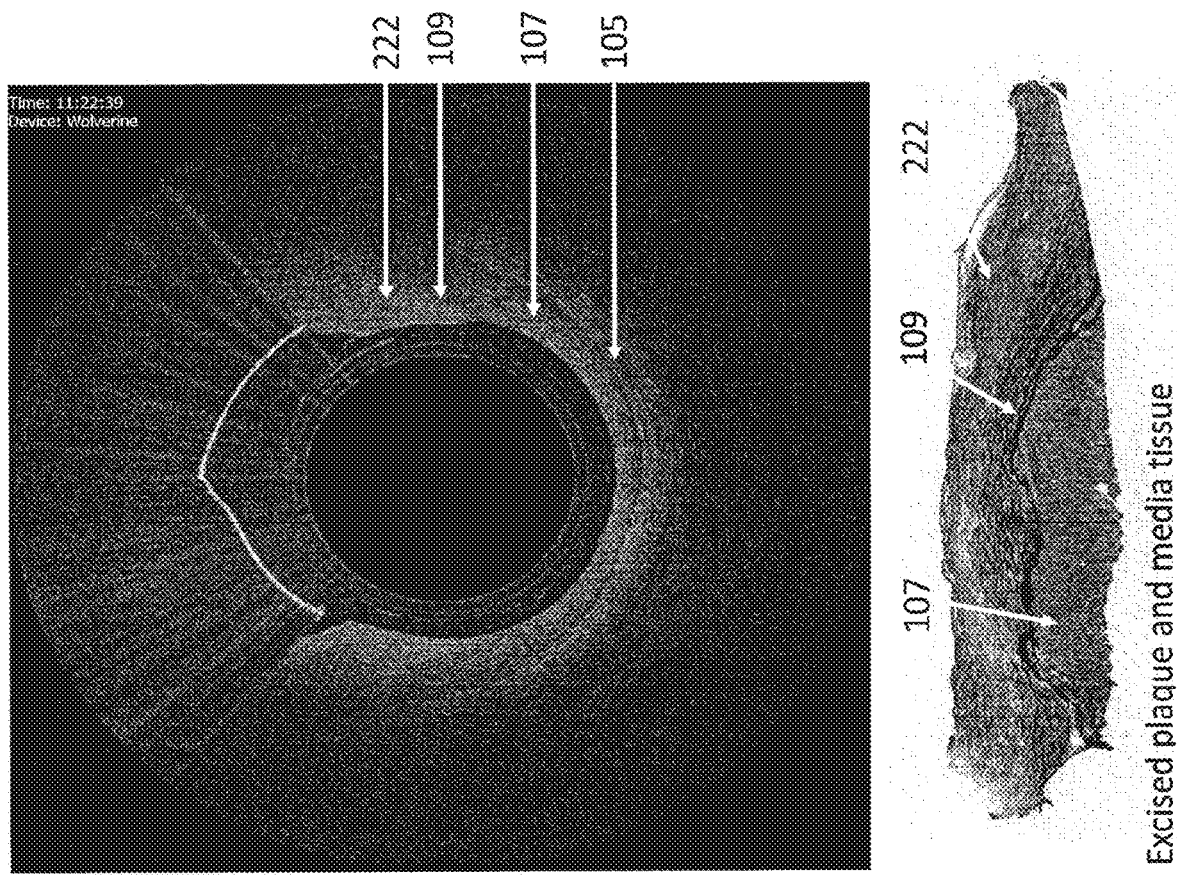

Referring to FIGS. 5a-5b, in one embodiment, the direction of the cut can be modified to avoid the EEL 105, i.e., the distal tip of the catheter 200 can be oriented away from the EEL 105. In some embodiments, markers on the image can be used to help orient the direction of the catheter to ensure that the EEL is not cut (i.e., the middle marker 333 can show a position directly opposite to the direction of the cut). The cutting direction can thus be changed from being oriented directly at the healthy artery wall (and thus normal to the EEL) and instead towards the plaque 333.

As a result of the direction and/or depth modifications, the tissue can be cut right up to, but not through, the EEL 105. FIGS. 6a-6h show the OCT image and resulting tissue cut using the identification methods described herein. As shown, only plaque tissue 222 (and the IEL 109 and media 107 in FIG. 6g) is cut, but not the EEL 105.

Figure 3A:
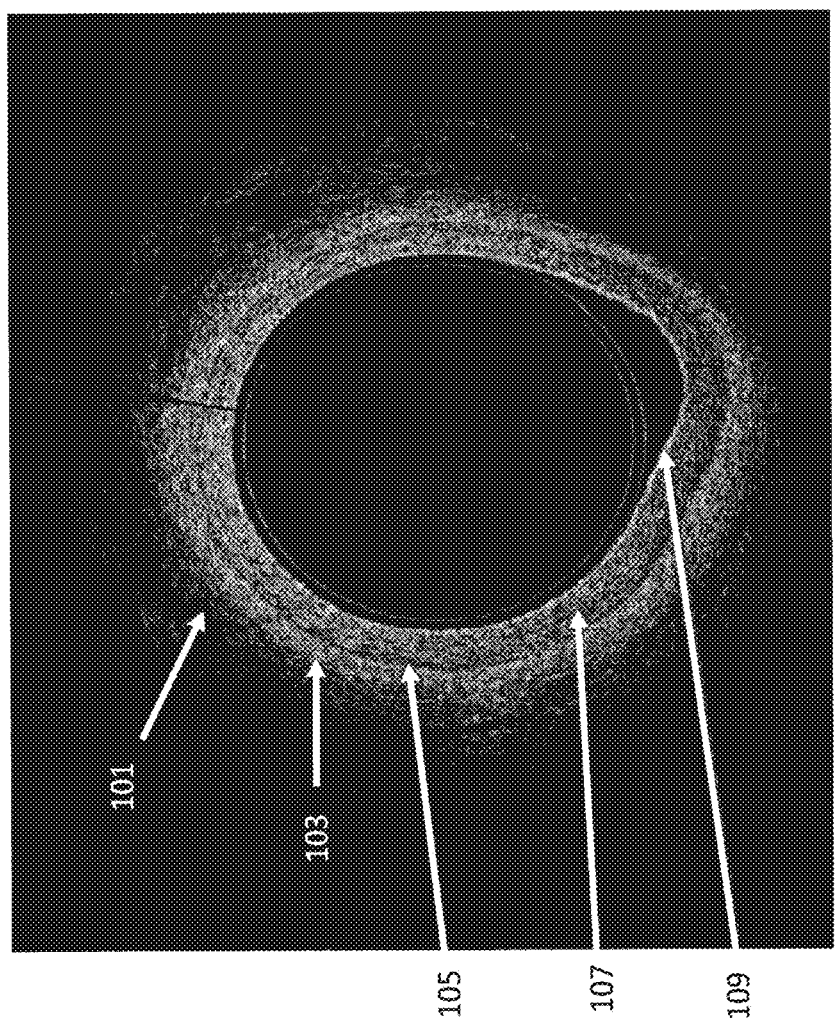
FIGS. 3a-3ii are exemplary OCT images wherein the internal elastic lamina and/or the external elastic lamina can be identified.
Figure 3C:
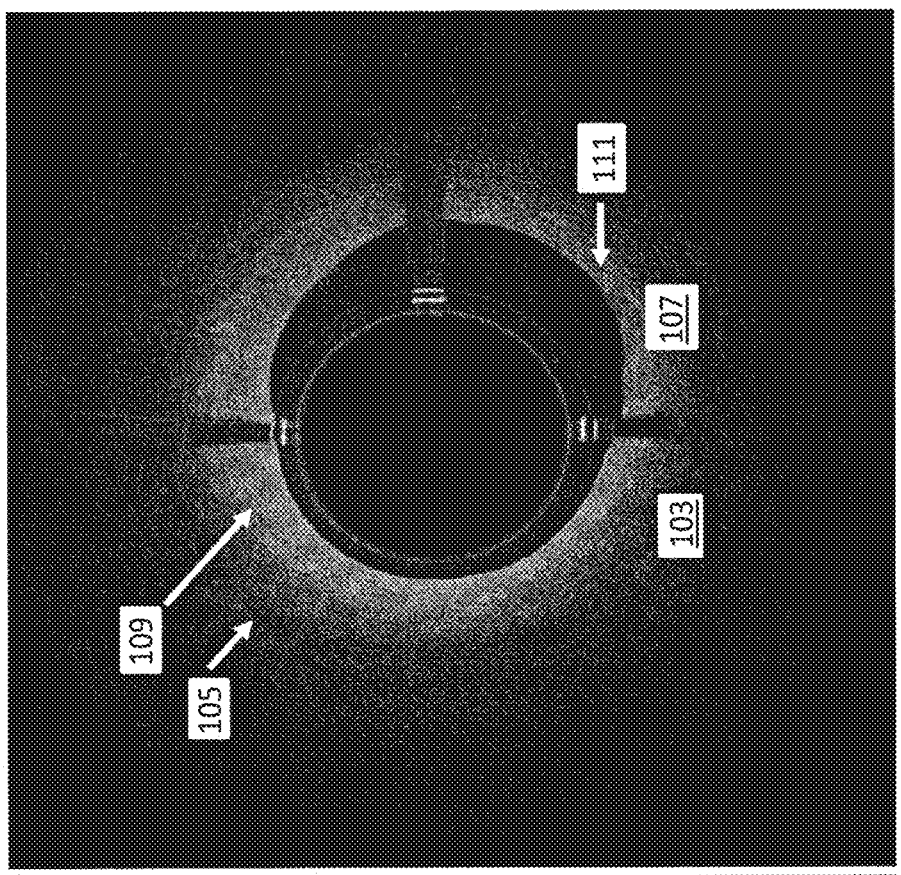
Figure 3B:
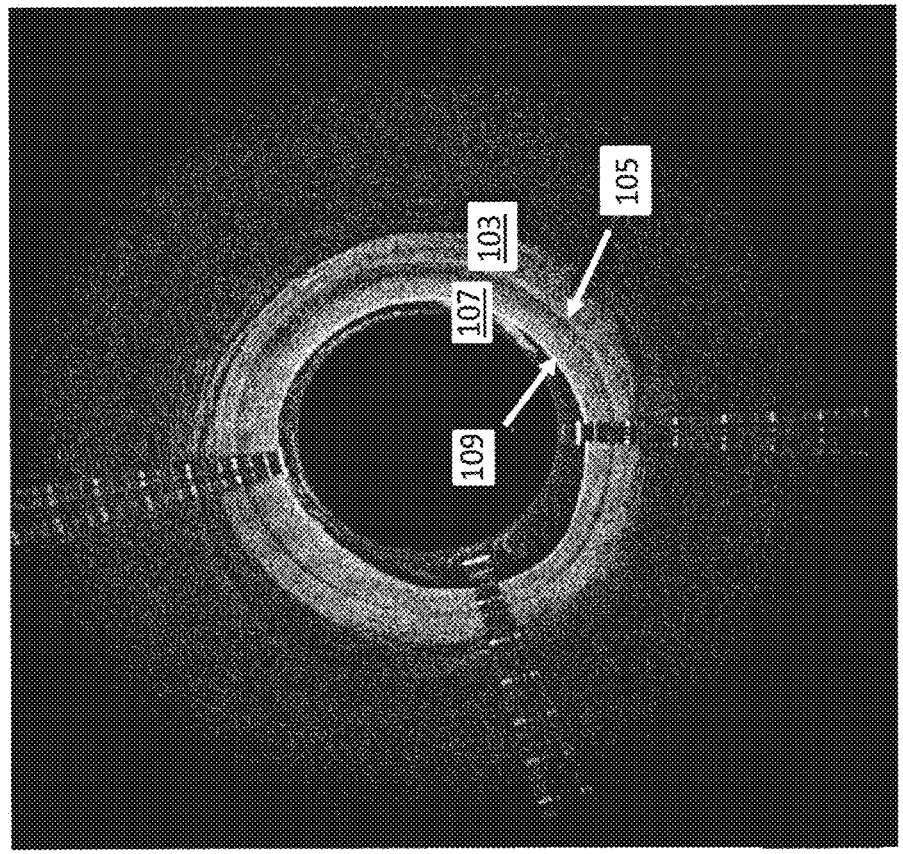
Figure 3E:
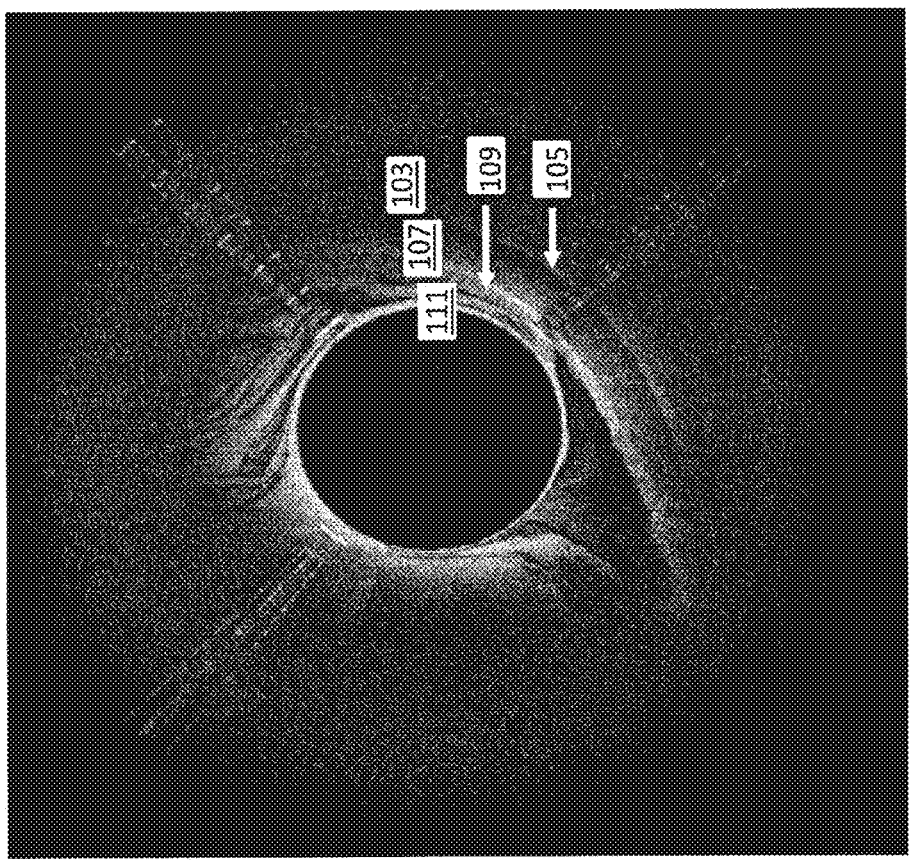
Figure 3D:
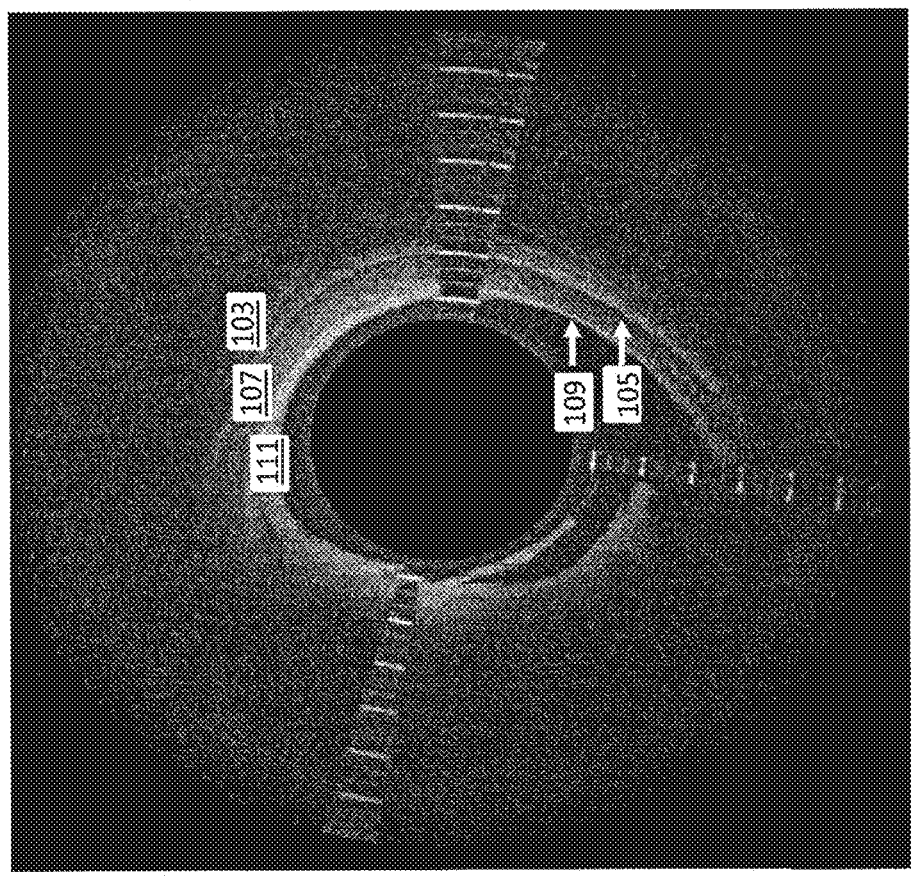
Figure 3G:
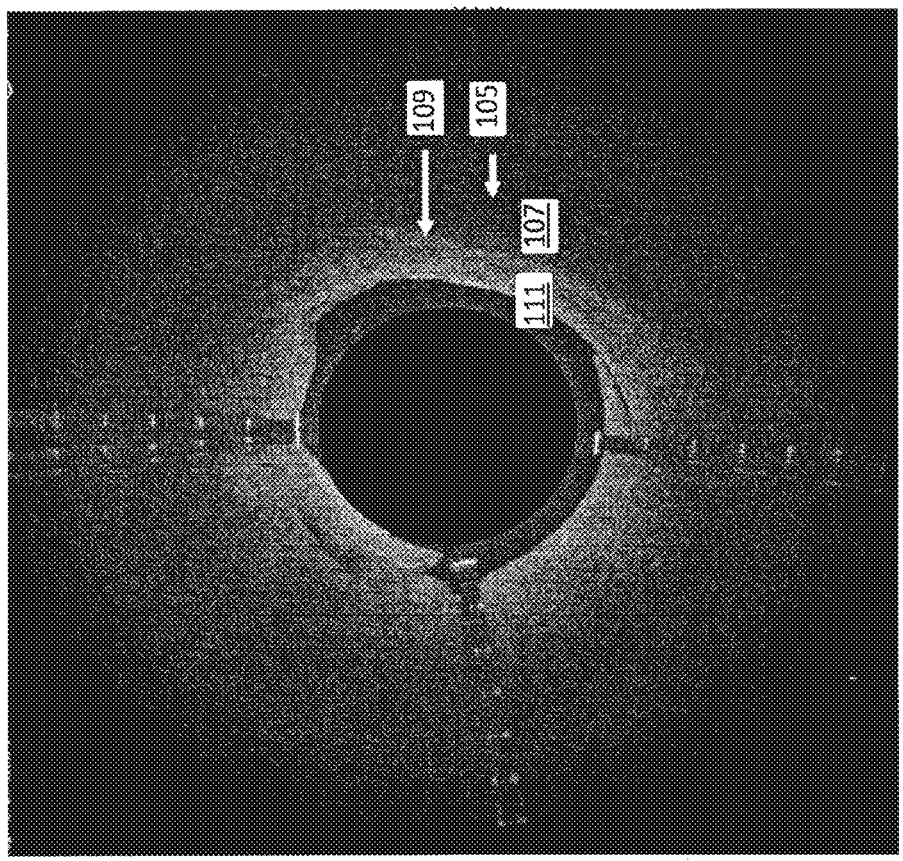
Figure 3F:
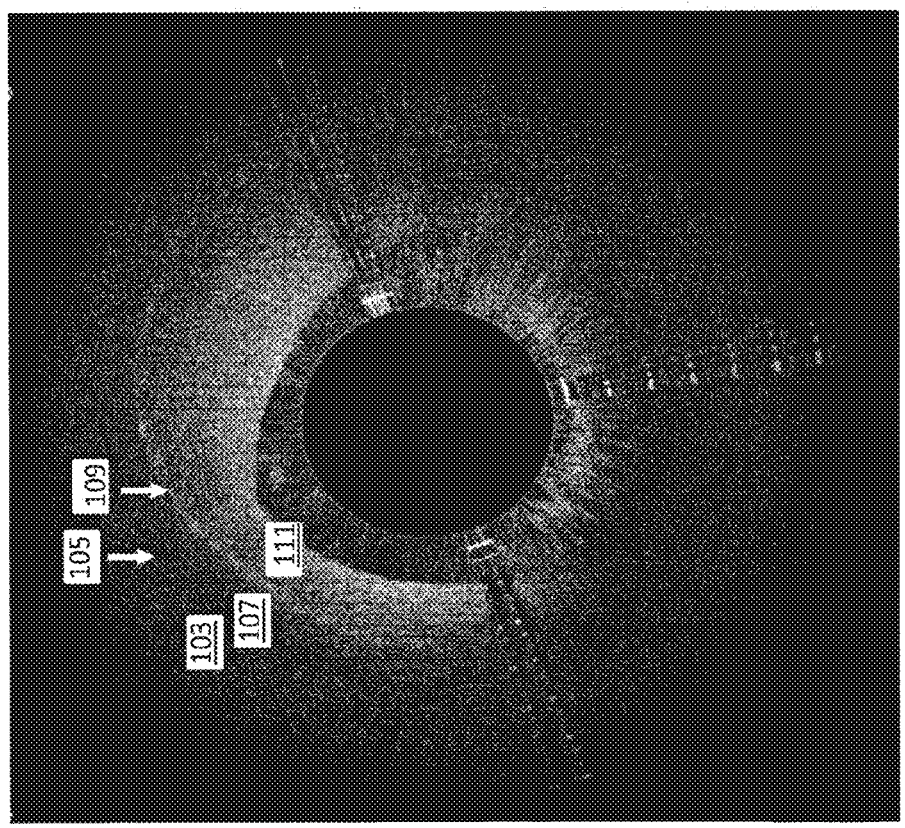
Figure 3I:
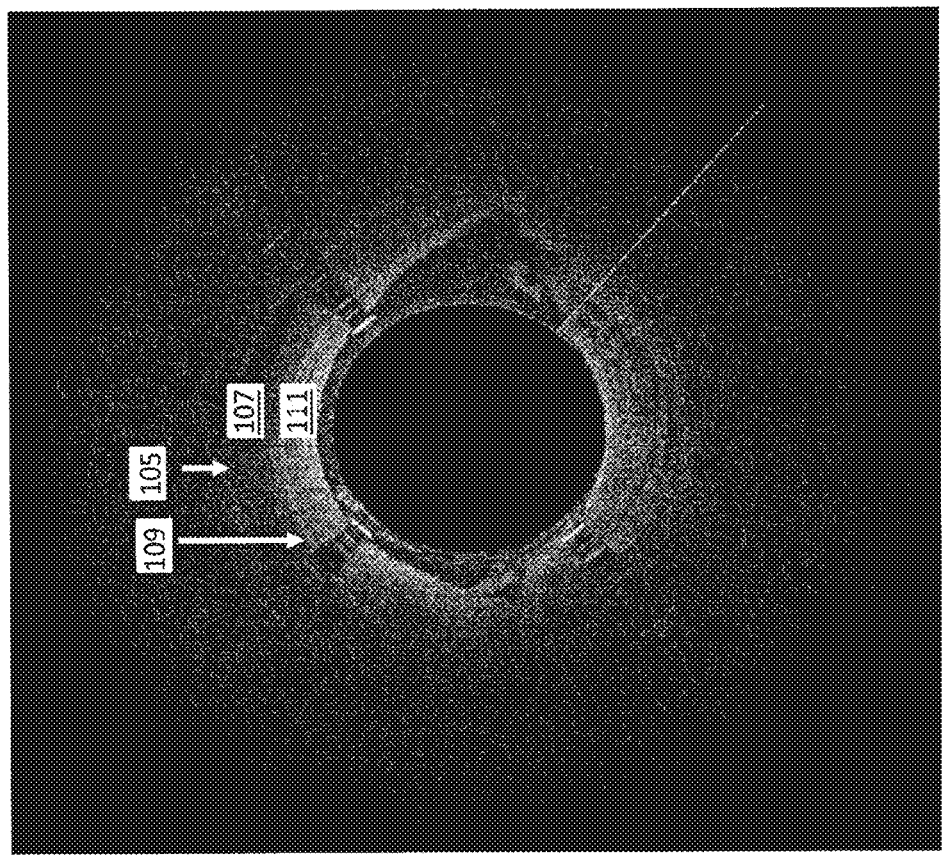
Figure 3H:
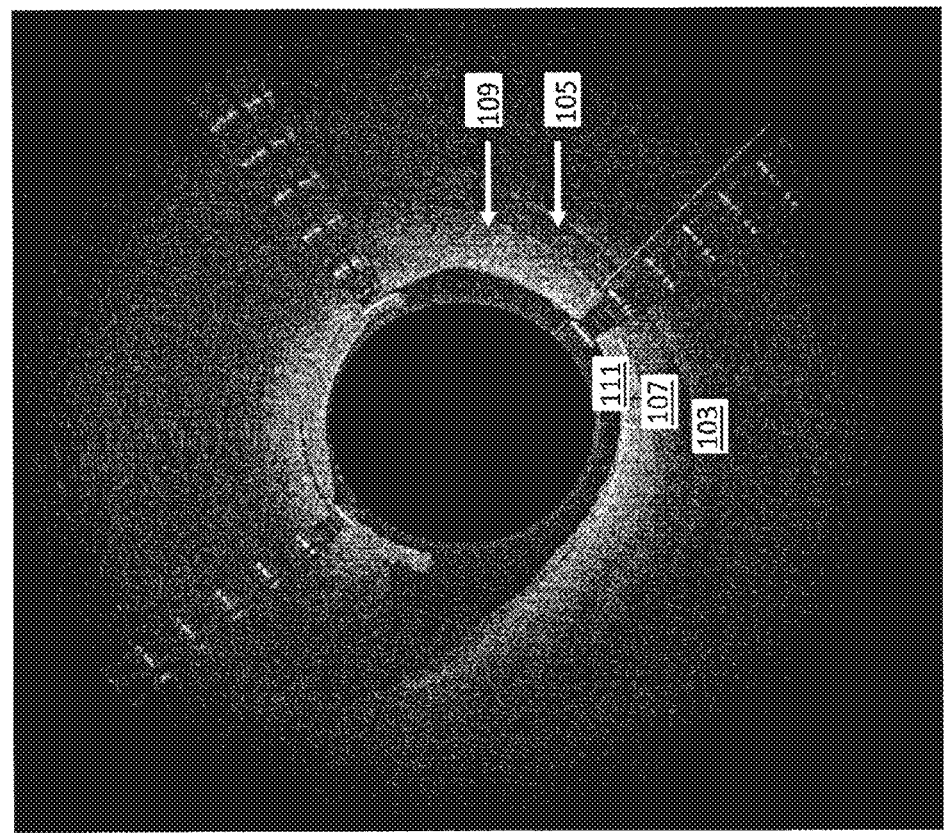
Figure 3M:
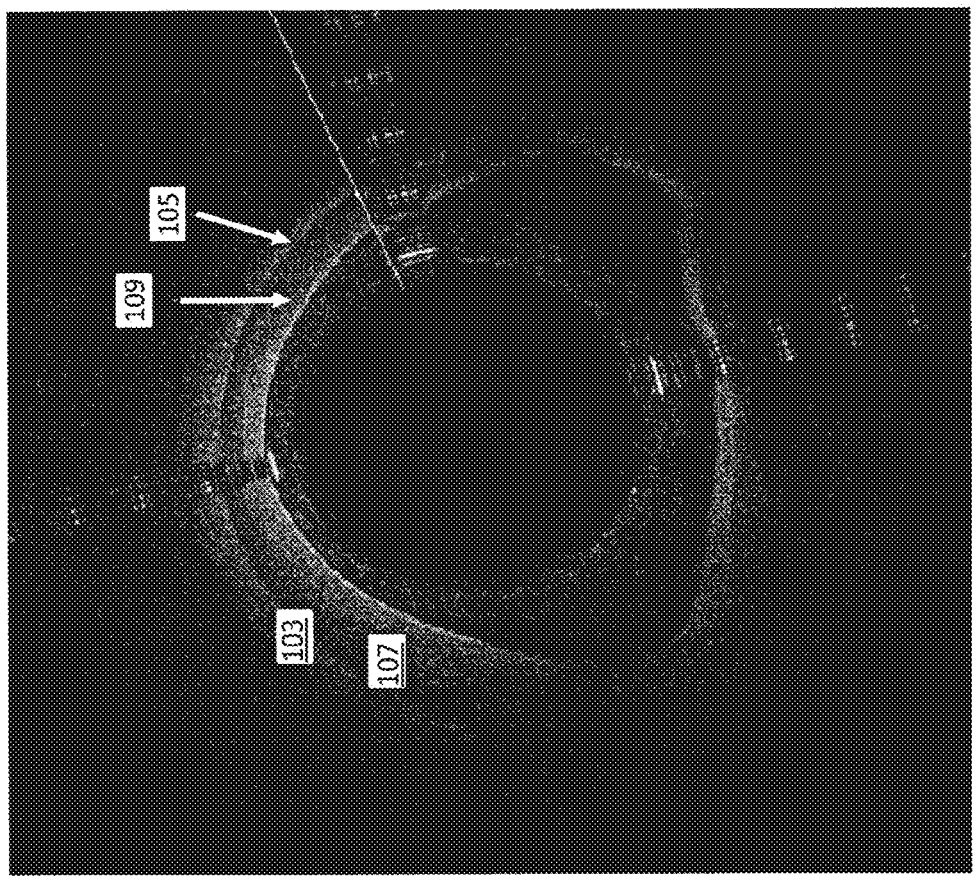
Figure 3L:
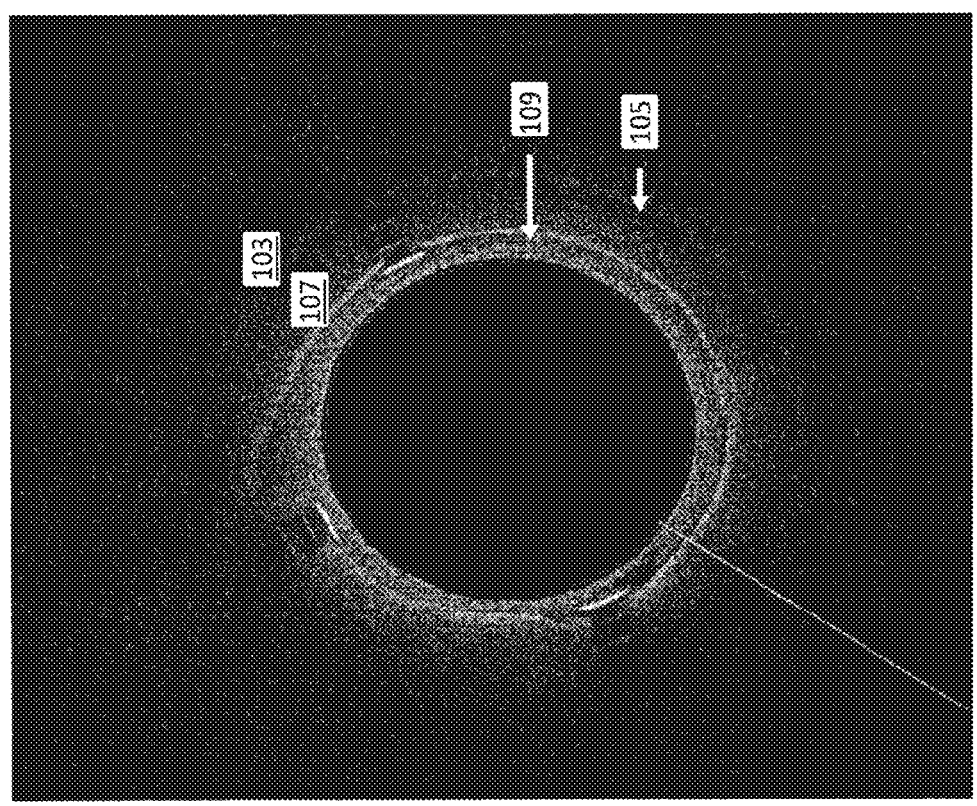
Figure 3O:
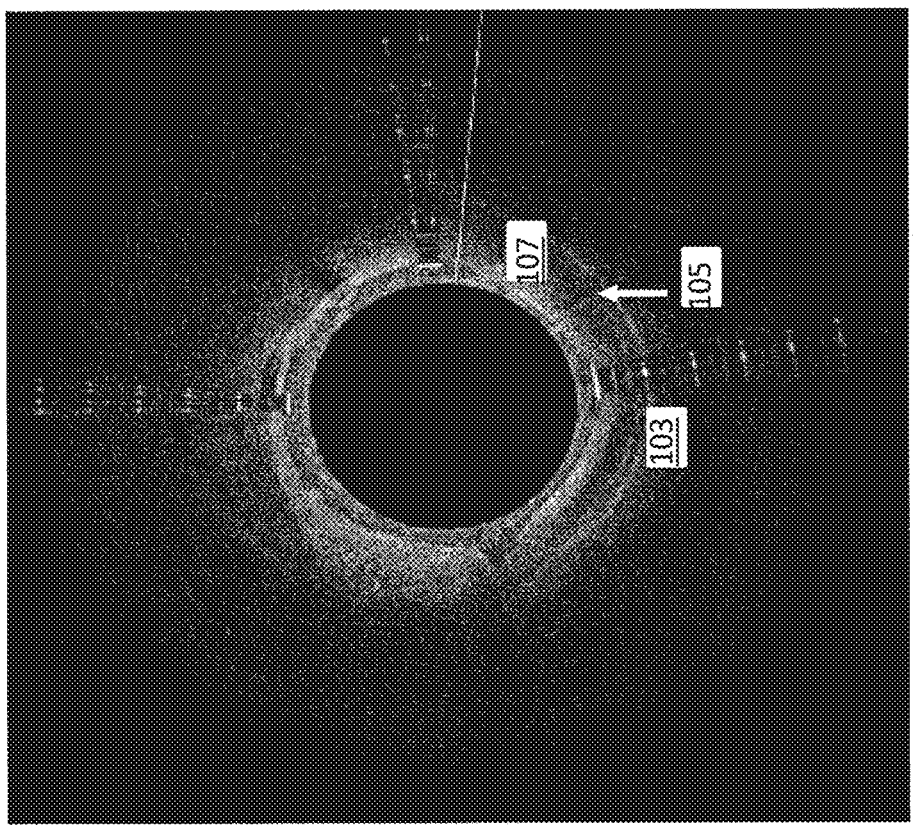
Figure 3N:
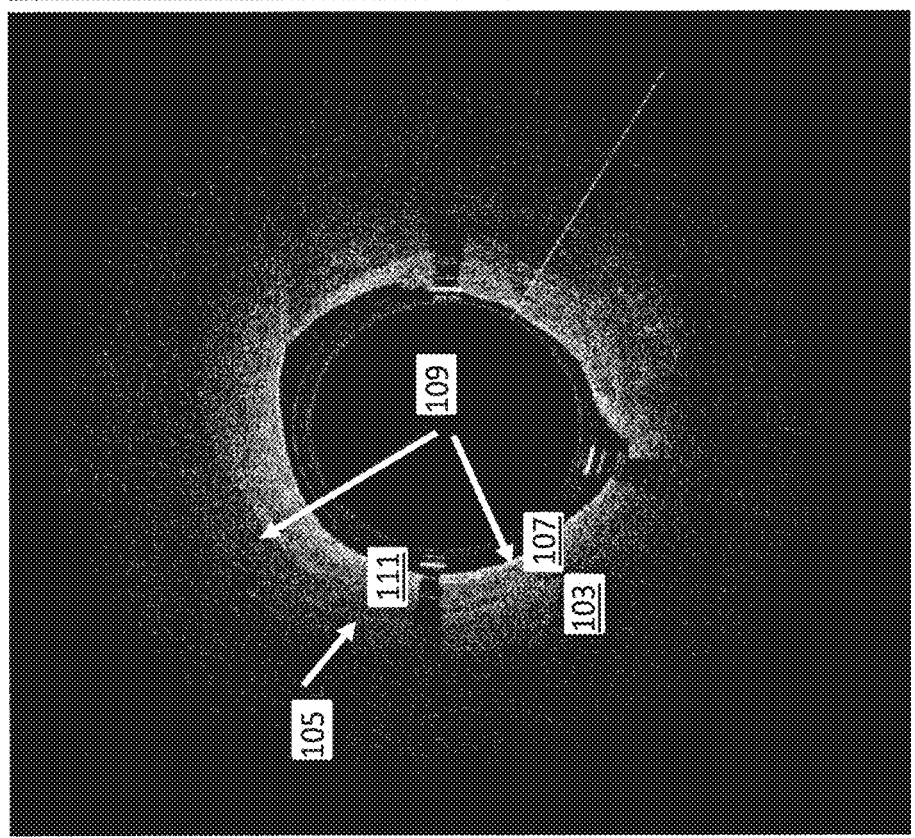
Figure 3Q:
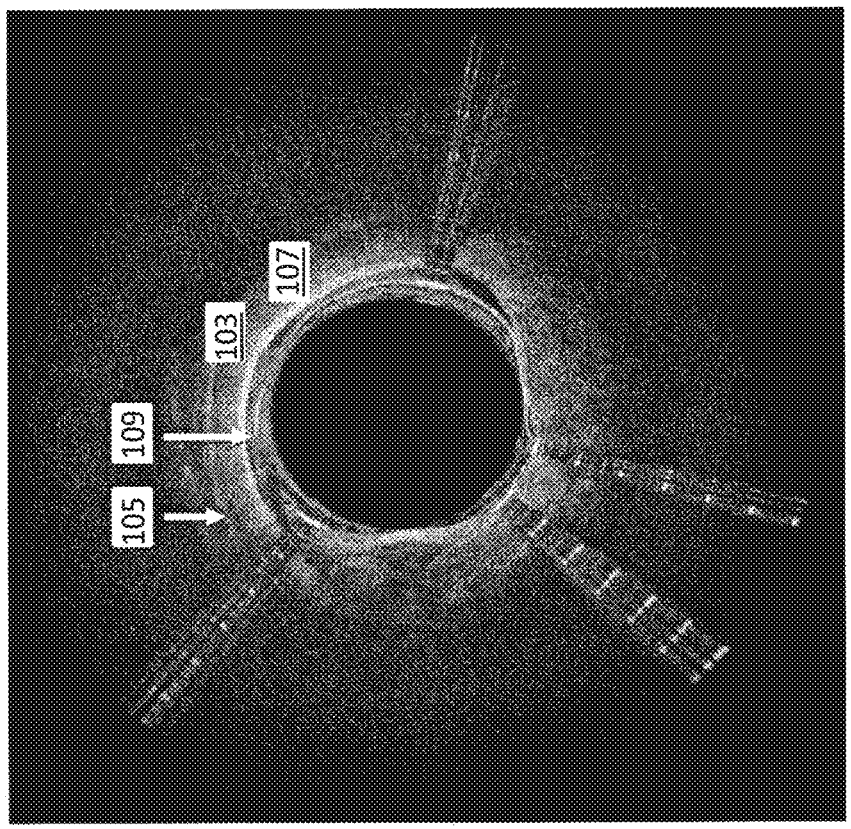
Figure 3P:
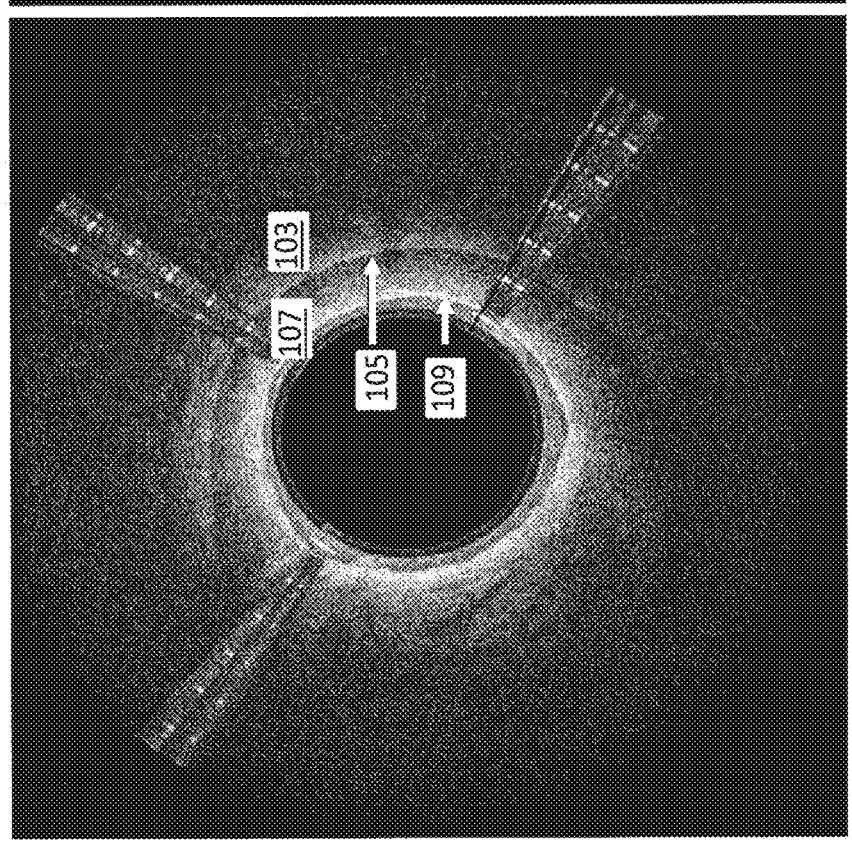
Figure 3S:
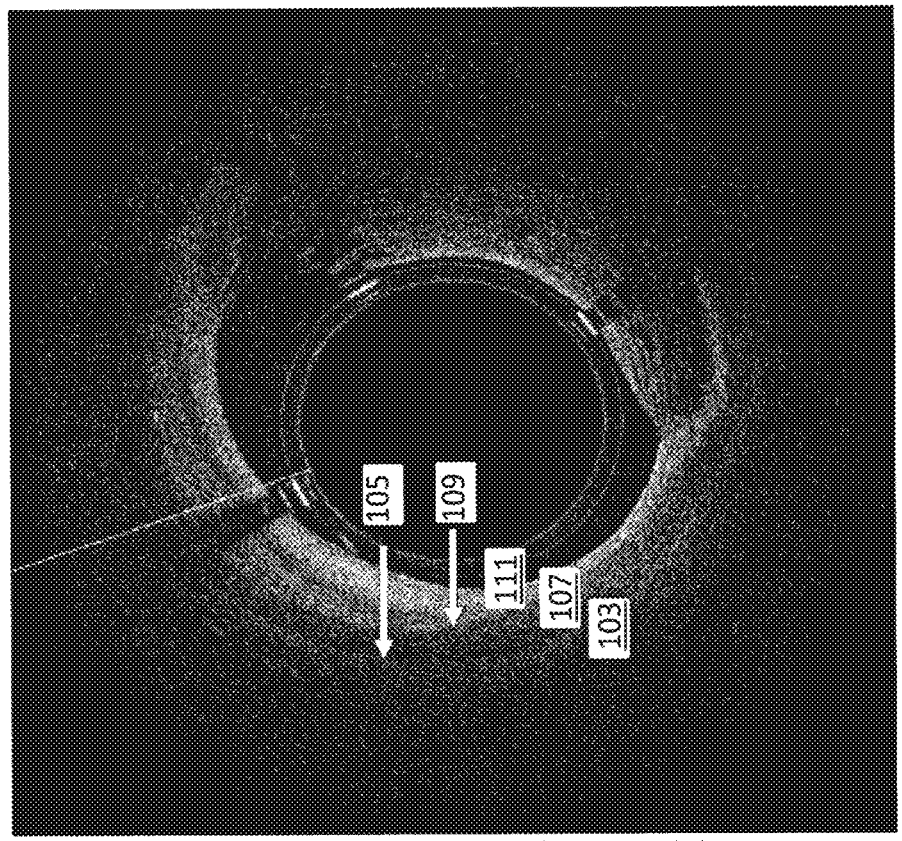
Figure 3R:
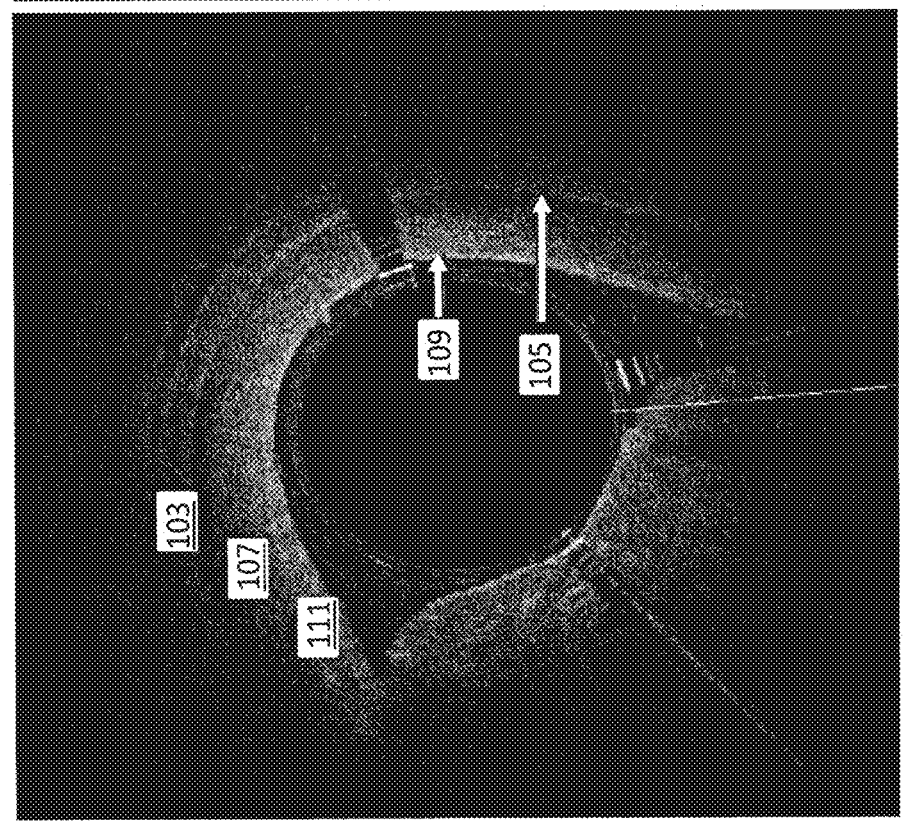
Figure 3W:
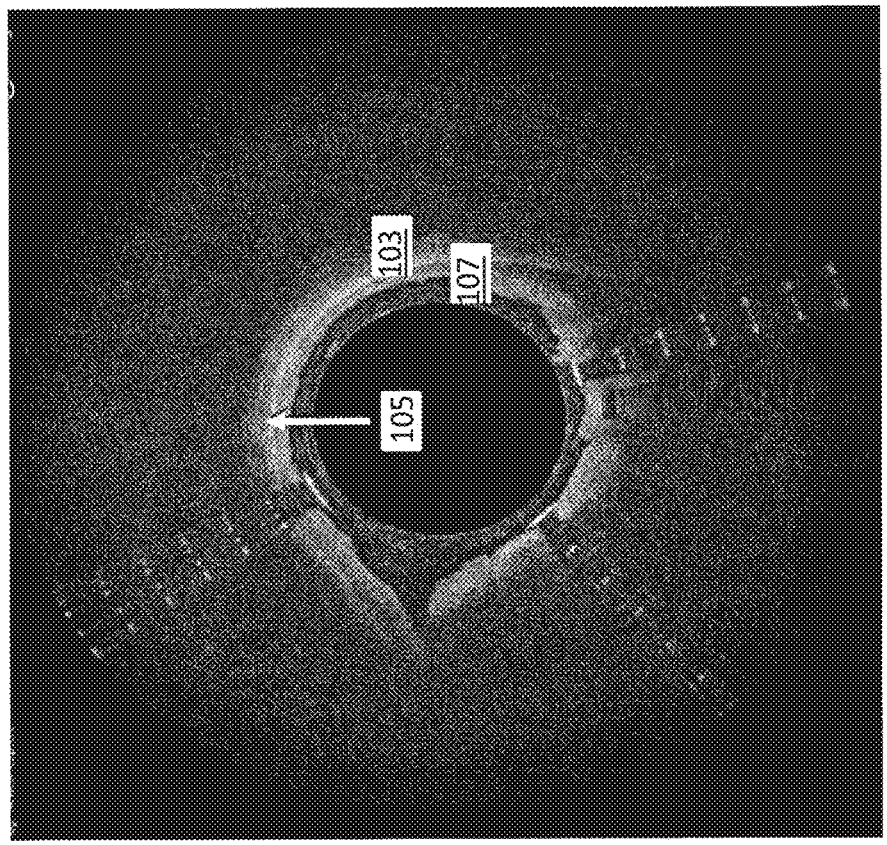
Figure 3V:
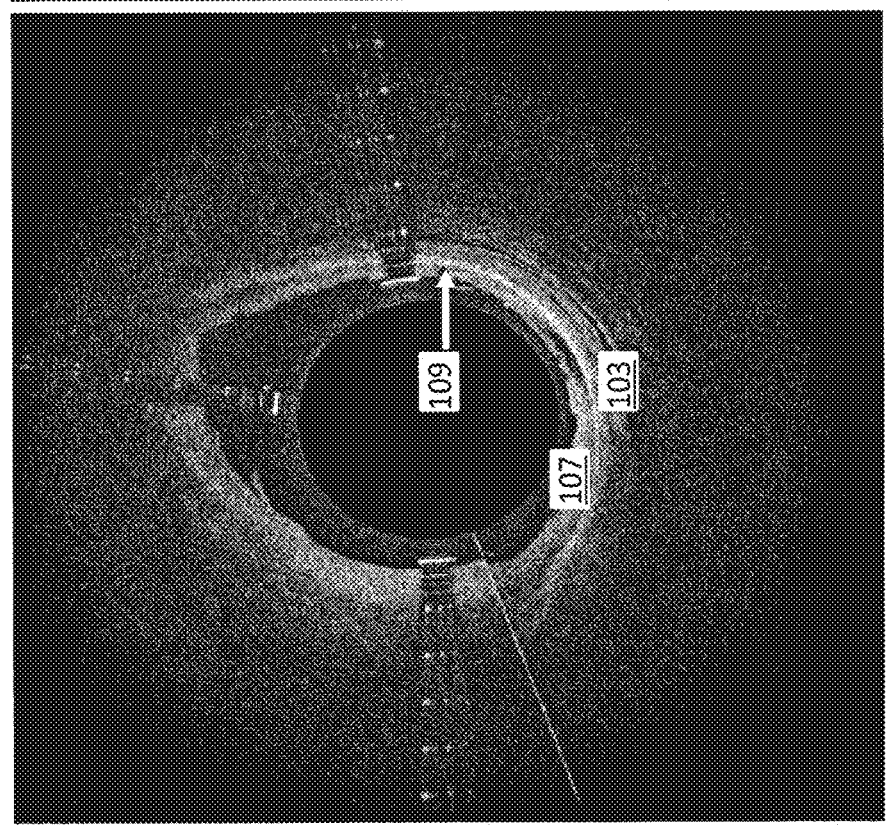
Figure 3Y:
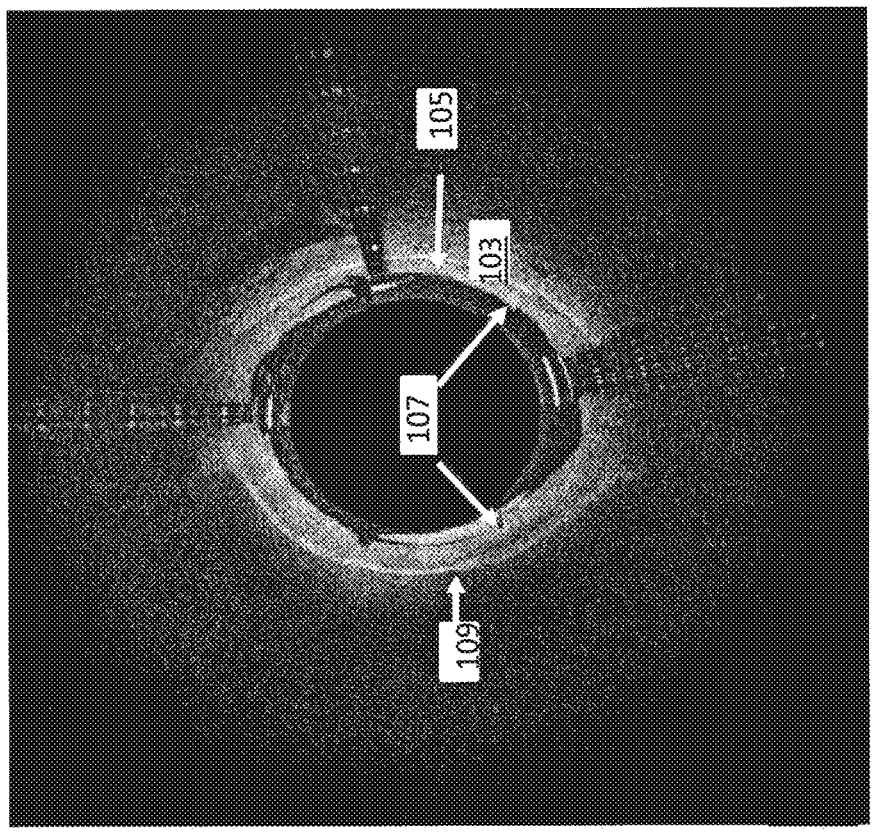
Figure 3X:
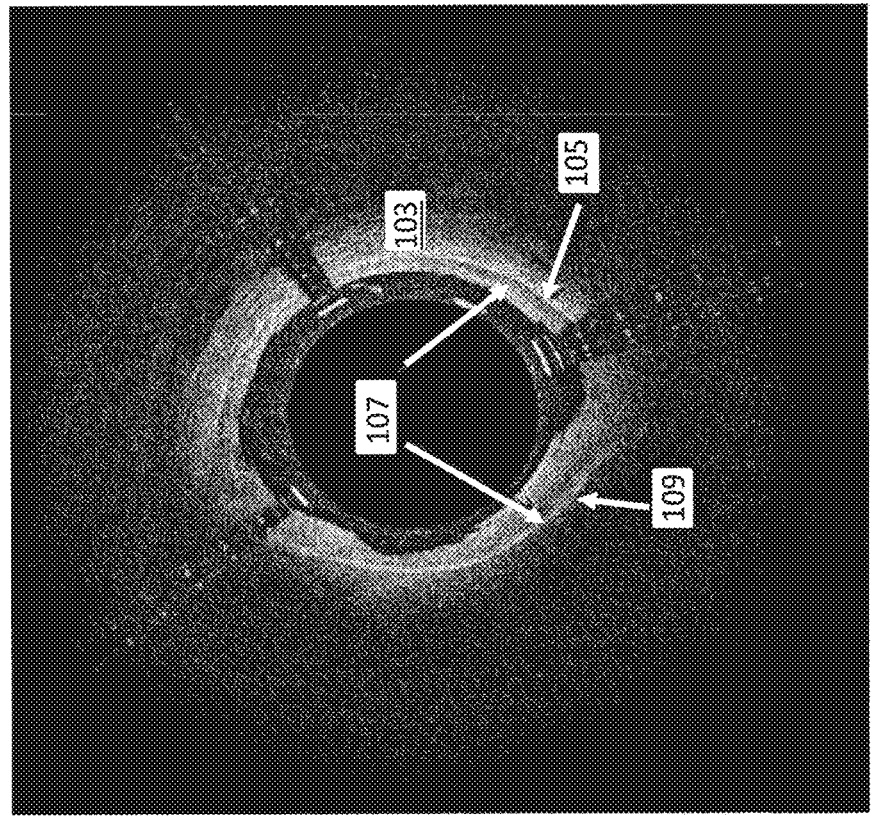
Figure 3A:
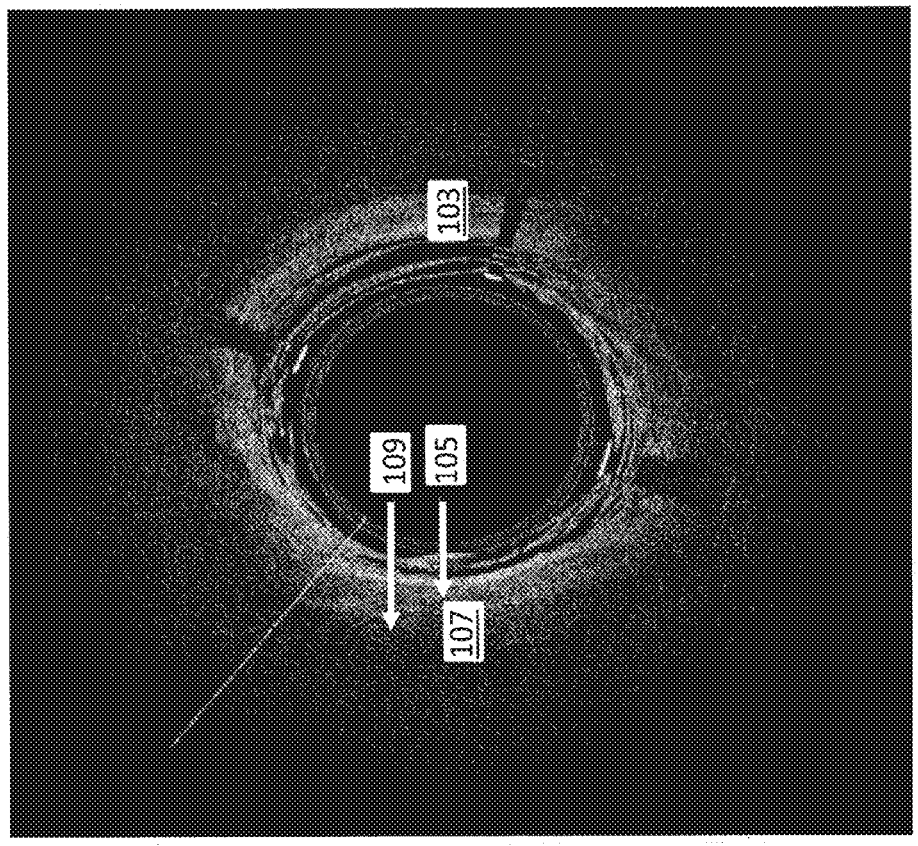
Figure 3Z:
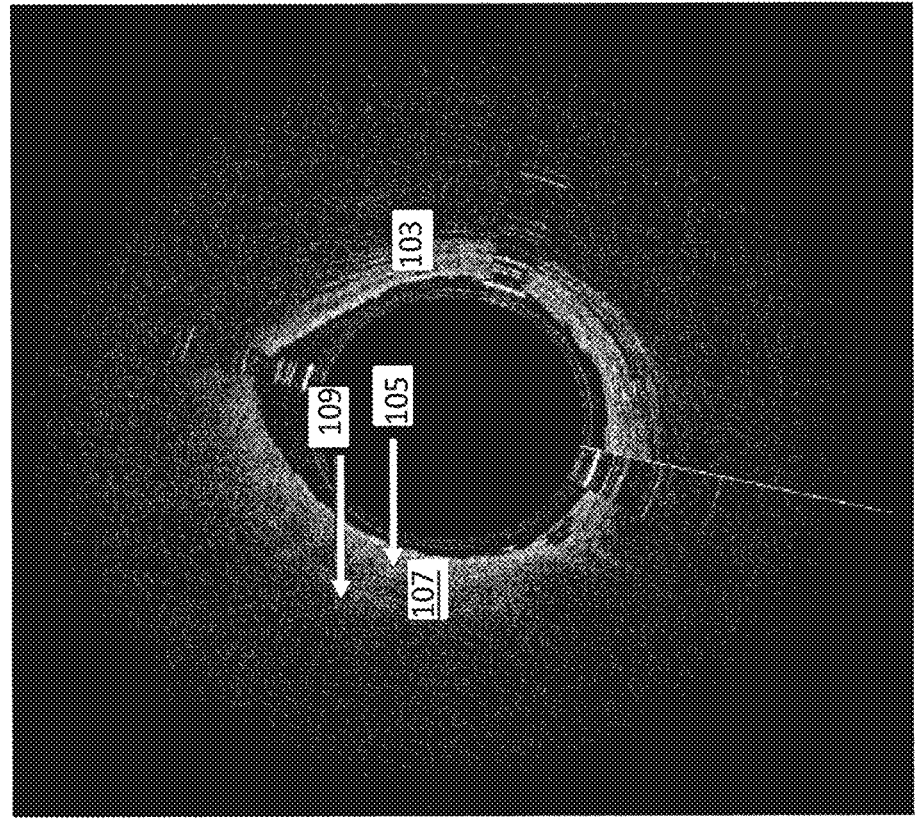
Figure 3C:
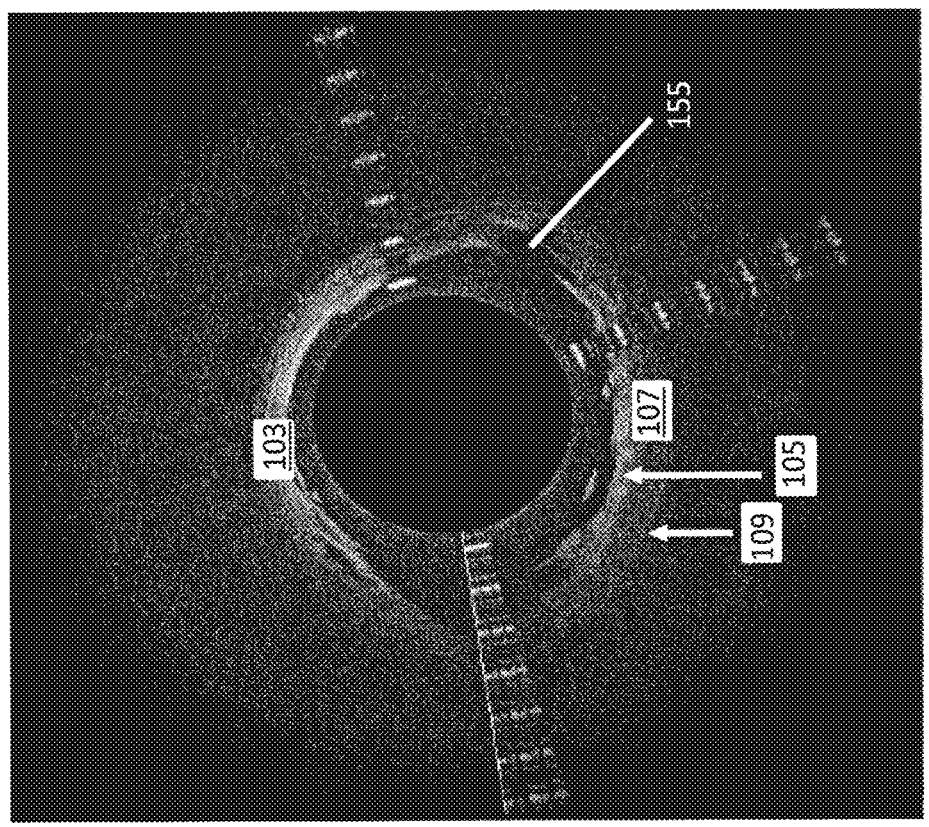
Figure 3B:
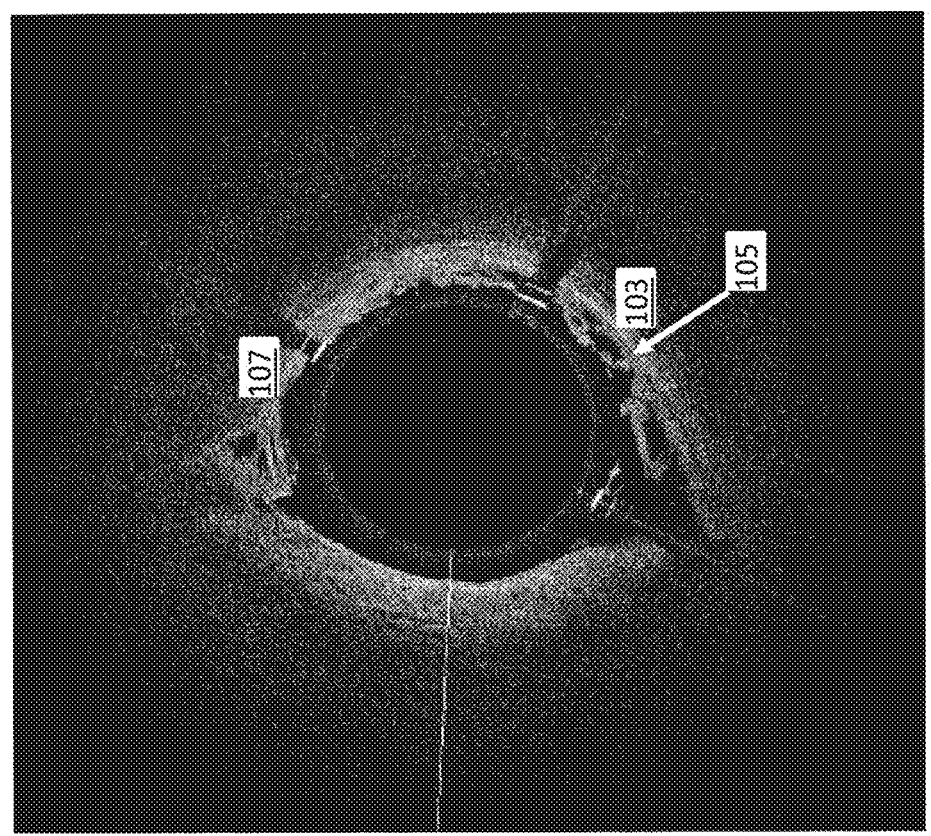
Figure 3G:
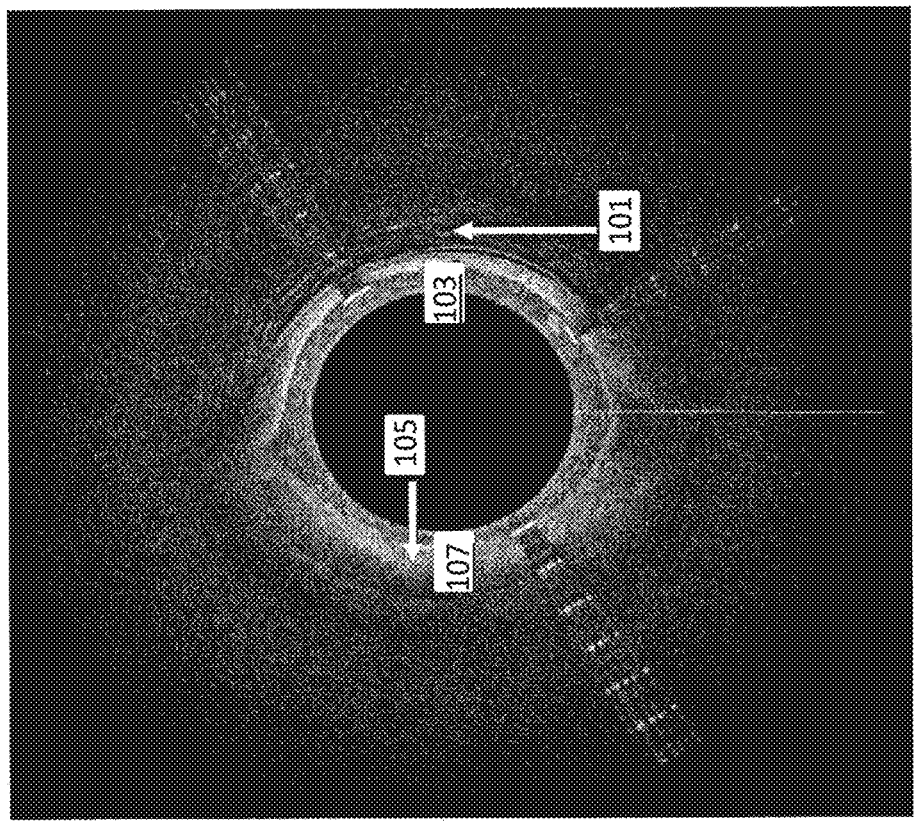
Figure 3F:
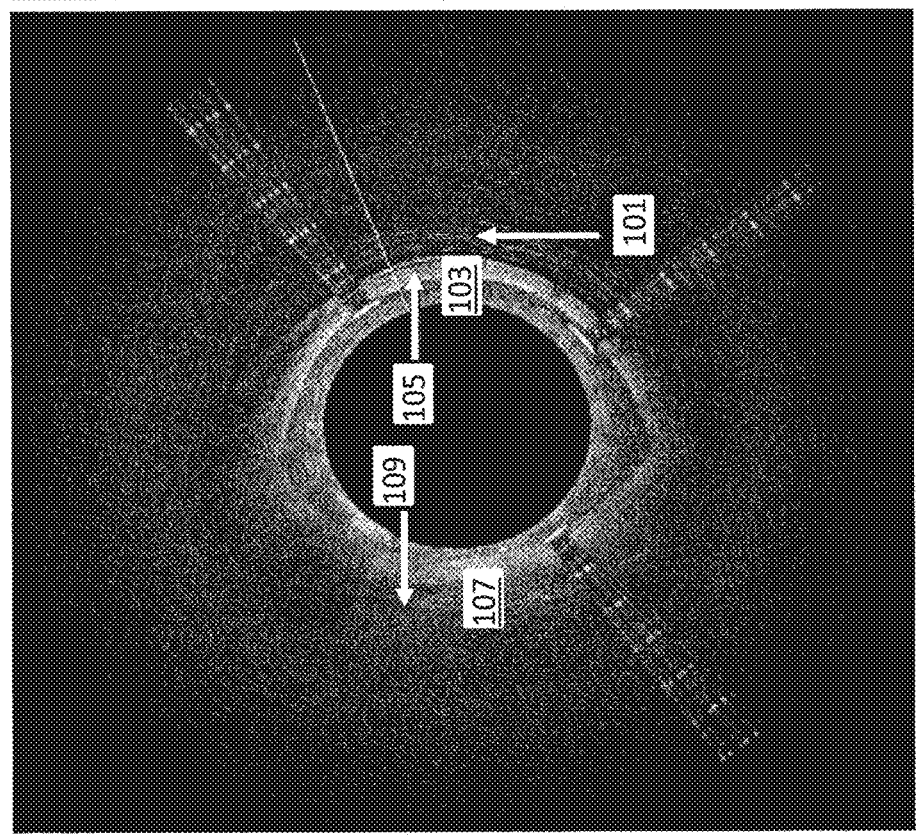
Figure 3I:
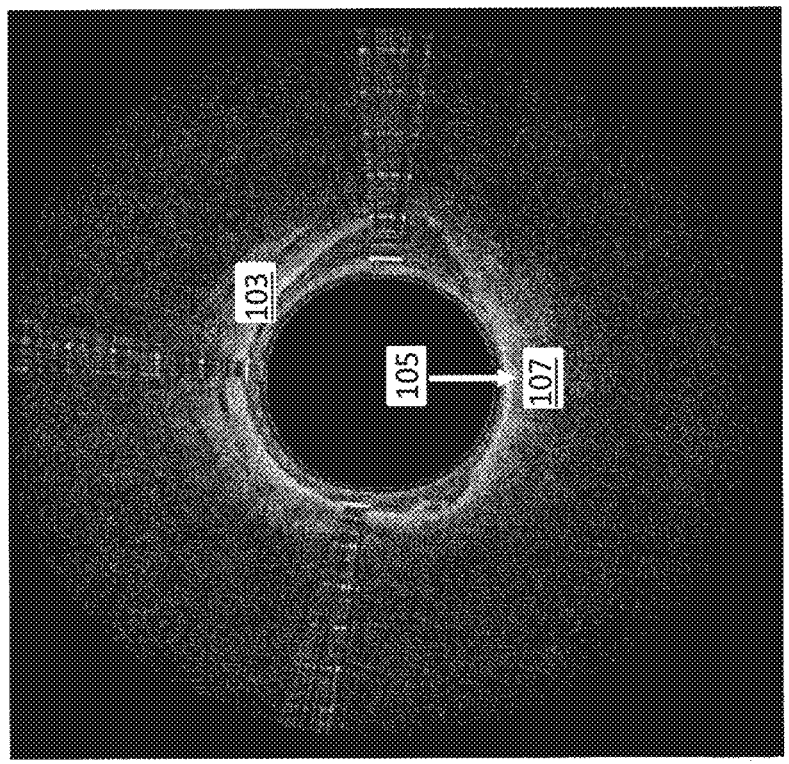
Figure 3H:
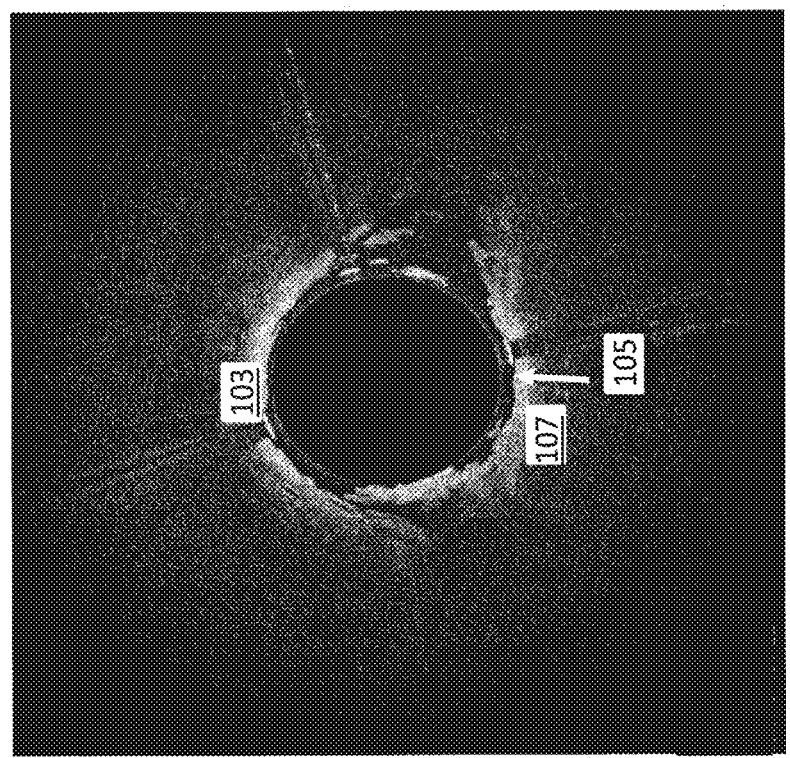

Moreover, if the OCT images show that trauma has occurred (i.e., if the images shown a break 155 in the continuity of the bright lines as shown in FIG. 3cc), the treatment plan can be adjusted so as to avoid further trauma, such as by reorienting the catheter or adjusting the depth of cut. Furthermore, if trauma to the EEL 105 is identified, the treatment plan can be adjusted to mitigate the inflammatory cascade by implanting drug coated stents, drug eluting balloons, or oral medication (e.g., anti-inflammatory, Plavix, etc.).

In some embodiments, the identification of the EEL 105 can be performed manually by a physician or technician viewing the imagines.

In other embodiments, the identification of the EEL 105 can be performed automatically with a controller. For example, referring to FIGS. 7a-7e, an A-line graph 717 of intensity vs. depth can be taken at an angle α within an OCT image 707. The peak intensity in the graph will correspond to the EEL 105 while the next highest peak will correspond to the IEL 109. The controller can then move to a new angle and search for the contour. For example, if the if the sector is unfolded into a B-scan 127, the EEL 105 can be identified at the set angle α and then the process repeated to find a continuous edge. As shown in FIG. 7d, if the line is continuous, it signifies the EEL 105. If it is discontinuous, then either the features is not the EEL or the EEL has been broken.

Figure 8:
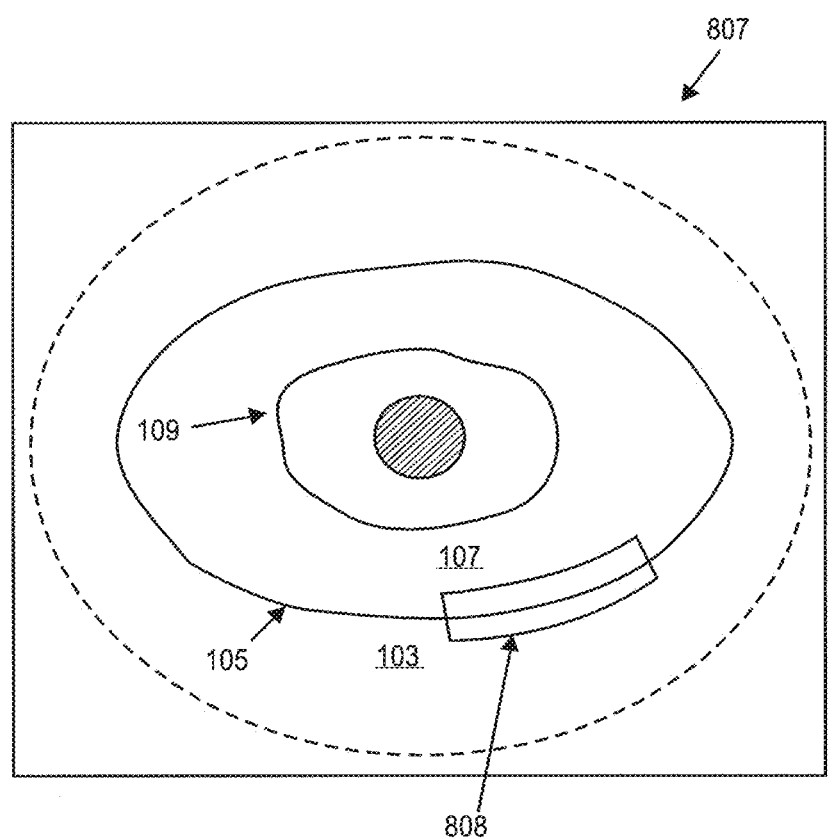
FIG. 8 shows an OCT image with a highlighted band on the EEL.

In some embodiments, the EEL can be automatically labeled or highlighted in the display of the OCT images. Referring to FIG. 8, the EEL 105 could be labeled in the OCT image 807, for example, with a transparent colored band 808. The band 808 can, for example, be brighter for greater confidence in EEL detection. The band 808 can further include different colors or widths, can be overlaid with different small shapes (such as dots or triangles). Further, the band 808 can be drawn outside of the OCT image 807 to identify where the feature is without interrupting the viewing (e.g., as an arc outside the OCT region).

Further, in some embodiments, a controller can use the identification of the EEL 105 to automatically assist with the interventional procedure. That is, in some embodiments, both the EEL 105 can be detected as well as the distance between the EEL and the cutter edge. The controller can thus calculate a distance between the EEL and the cutter and take a set action if that distance goes below a threshold value. For example, the controller can set off an alarm (e.g., audible noise, flash of light, graphic symbol). In other embodiments, the controller can shut down the cutter activation if the distance is below the threshold (and/or if the EEL 105 is going to be or has been broken or damaged as shown in FIG. 7e). In still other embodiments, the amount of urge on the catheter can be automatically reduced (such as the amount of balloon inflation). To automatically reduce the amount of urge, the inflation/deflation of the balloon, and thus the movement of the cutter between an active (or open) position to a passive (or closed) position can be automated with servos (or motors, or actuators) that are controlled by the controller. The controller can thus use the identification of the EEL 105 to partially or completely deflate the balloon, thereby reducing the cut depth and/or moving the cutter from an active to a passive position.

By identifying the EEL in images taken during interventional therapy, injury or trauma to those structures can advantageously be avoided. For example, referring to FIGS. 6a-4h, tissue cut during an atherectomy procedure using such techniques can advantageously include substantially only the diseased thrombosis or plaque (little to no media 107, adventitia 103, or EEL 105). In contrast, in atherectomy procedures where such methods are not used, excised tissue can include EEL 105, media 107, and/or adventitia 103, in addition to the diseased tissue, suggesting that an enhanced inflammatory response was instigated during the atherectomy procedure.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

The invention claimed is:

1. A method of performing atherectomy, comprising:
   inserting an atherectomy device into a vessel of a patient;
   gathering optical coherence tomography (OCT) images using an imaging sensor on the device;
   identifying an external elastic lamina (EEL) of a wall of the vessel in the OCT images;
   orienting a cutter of the atherectomy device away from the EEL based upon the identifications;
   adjusting a depth of cut based upon the identification; and
   removing plaque from the wall of the vessel with the cutter while the cutter is oriented away from the EEL;
   wherein the device further includes a balloon configured to inflate or deflate to expose or cover the cutter, and wherein moving the cutter from an active mode to a passive mode comprises at least partially deflating the balloon.

2. The method of claim 1, wherein orienting the cutter of the atherectomy device away from the EEL comprises moving the cutter from a direction normal to the EEL to a direction towards the plaque.

3. The method of claim 1, further comprising determining from the OCT images whether trauma to the EEL has occurred.

4. The method of claim 3, further comprising adjusting a treatment plan to mitigate an inflammatory cascade caused by the trauma to the EEL.

5. The method of claim 4, wherein adjusting the treatment plan comprises implanting a drug coated stent in the vessel, implanting a drug eluting balloon in the vessel, or providing an oral medication to the patient.

6. The method of claim 1, wherein the OCT images are a toroidal view of the vessel.

7. The method of claim 6, wherein the step of identifying an EEL further comprises identifying an outer-most bright line in the toroidal view.

8. The method of claim 1, wherein the adjusting step is performed automatically.

9. The method of claim 1, further comprising determining a distance between the cutter and the EEL.

10. The method of claim 9, further comprising activating an alarm if the distance is below a threshold value.

11. The method of claim 9, further comprising stopping removing plaque if the distance is below a threshold value.

* * * * *